(12) United States Patent
Green et al.

(10) Patent No.: US 6,838,050 B1
(45) Date of Patent: Jan. 4, 2005

(54) METHODS AND DEVICES FOR PROVIDING ANTI-INFECTIVE ACTIVITY TO A MEDICAL DEVICE

(75) Inventors: Terrence R. Green, Lake Oswego, OR (US); Jack Fellman, McMinville, OR (US)

(73) Assignee: Oxibio, Inc., Portland, OR (US)

(*) Notice: Subject to any disclaimer, the term of this patent is extended or adjusted under 35 U.S.C. 154(b) by 652 days.

(21) Appl. No.: 09/585,911

(22) Filed: Jun. 2, 2000

Related U.S. Application Data

(60) Provisional application No. 60/165,394, filed on Nov. 12, 1999, and provisional application No. 60/137,654, filed on Jun. 4, 1999.

(51) Int. Cl.[7] ................................................. A61L 2/00

(52) U.S. Cl. .................................... 422/37; 128/207.14

(58) Field of Search ............................... 422/1, 29, 37, 422/40; 604/265, 264, 890.1; 128/207.14

(56) References Cited

U.S. PATENT DOCUMENTS

| | | | |
|---|---|---|---|
| 1,867,222 A | 7/1932 | Karns .......................... 604/304 |
| 2,355,231 A | 8/1944 | Moore .......................... 205/701 |
| 4,093,610 A | 6/1978 | Abraham et al. ........ 260/112.5 |
| 4,278,548 A | 7/1981 | Bettinger et al. ........... 210/636 |
| 4,312,833 A | 1/1982 | Clough et al. ............... 422/30 |
| 4,476,108 A | 10/1984 | Kessler et al. ................ 424/50 |
| 4,576,817 A | 3/1986 | Montgomery et al. ........ 424/94 |
| 4,769,013 A | * 9/1988 | Lorenz et al. .............. 604/265 |
| 4,937,072 A | 6/1990 | Kessler et al. ............. 424/94.4 |
| 5,128,136 A | 7/1992 | Bentley et al. .............. 424/443 |
| 5,227,161 A | 7/1993 | Kessler ...................... 424/94.4 |
| 5,232,914 A | 8/1993 | Fellman ....................... 514/23 |
| 5,357,636 A | 10/1994 | Dresdner, Jr. et al. ....... 2/161.7 |
| 5,370,815 A | 12/1994 | Kessler ....................... 252/106 |
| 5,411,550 A | * 5/1995 | Herweck et al. ........... 623/1.27 |
| 5,419,816 A | 5/1995 | Sampson et al. ........... 205/556 |
| 5,419,902 A | 5/1995 | Kessler ...................... 424/94.4 |
| 5,447,505 A | 9/1995 | Valentine et al. ............ 604/304 |
| 5,462,713 A | 10/1995 | Schlitzer et al. .............. 422/37 |
| 5,492,911 A | 2/1996 | Stief ........................ 514/234.2 |
| 5,512,055 A | * 4/1996 | Domb et al. ................. 604/265 |
| 5,558,881 A | 9/1996 | Corby |
| 5,562,652 A | * 10/1996 | Davis ....................... 604/890.1 |
| 5,607,681 A | 3/1997 | Galley et al. ................ 424/405 |
| 5,629,024 A | 5/1997 | Kessler et al. .............. 424/667 |
| 5,648,075 A | 7/1997 | Kessler et al. |
| 5,679,399 A | 10/1997 | Shlenker et al. ............. 427/2.3 |
| 5,695,458 A | * 12/1997 | Shikani et al. ............. 604/4.01 |
| 5,698,738 A | 12/1997 | Garfield et al. ............. 564/112 |
| 5,705,050 A | 1/1998 | Sampson et al. ........... 205/687 |
| 5,747,058 A | 5/1998 | Tipton et al. ............... 424/423 |
| 5,762,638 A | * 6/1998 | Shikani et al. ............. 604/265 |
| 5,772,971 A | 6/1998 | Murphy et al. ............. 422/292 |
| 5,948,385 A | * 9/1999 | Chapman et al. .......... 424/1.29 |
| 5,951,458 A | * 9/1999 | Hastings et al. ............... 600/3 |
| 5,965,276 A | 10/1999 | Shlenker et al. ............ 428/492 |
| 5,968,542 A | 10/1999 | Tipton ....................... 424/423 |
| 5,997,468 A | * 12/1999 | Wolff et al. .................... 600/36 |
| 6,362,156 B1 | 3/2002 | Hsu et al. .................... 510/418 |
| 6,482,309 B1 | * 11/2002 | Green et al. ................. 205/619 |
| 6,592,890 B1 | 7/2003 | Green ......................... 424/447 |

FOREIGN PATENT DOCUMENTS

| | | |
|---|---|---|
| EP | 0 747 062 | 12/1996 |
| GB | 0382572 | 10/1932 |
| JP | 083104573 | 12/1984 |
| WO | 8502422 | 6/1985 |
| WO | WO 93/24132 | 12/1993 |
| WO | 9426317 | 11/1994 |
| WO | 9507691 | 3/1995 |
| WO | WO 95/12316 | 5/1995 |
| WO | WO 96/20019 | 7/1996 |
| WO | WO 96/38548 | 12/1996 |
| WO | 9805689 | 2/1998 |
| WO | WO 99/65538 | 12/1999 |
| WO | 0054593 | 9/2000 |
| WO | 0074743 | 12/2000 |
| WO | 0128598 | 4/2001 |
| WO | 0128600 | 4/2001 |

OTHER PUBLICATIONS

Barabas et al., "Providone–Iodine", *Analytical Profiles of Drug Substances and Excipients*, 25, 342–462, (1998).

Birnbaum et al., "The Role of Iodine–Releasing Silicone Implants in Prevention of Spherical Contractures in Mice", *Plastic and Reconstructive Surgery*, 69 (6), 956–959 (1982).

Caufield et al., "In Vitro Susceptibility of Streptococcus mutans 6715 to Iodine and Sodium Fluoride, Singly and in Combination, at Various pH Values", *Antimicrobial Agents and Chemotherapy*, 22 (1), 115–119 (1982).

Conn et al., "Iodine Disinfection of Hydrophilic Contact Lenses", *annals of Ophthalmolgy*, 361–363, (1981).

J. Gordon, "Opening Address", *Postgrad Med. J.*, 69 (suppl. 3), S1–S3, (1993).

(List continued on next page.)

Primary Examiner—Krisanne M. Thornton
(74) Attorney, Agent, or Firm—Heller Ehrman White & McAuliffe LLP

(57) ABSTRACT

Methods of providing anti-infective activity to a medical device including the steps of exposing the medical device to an anti-infective oxidant, and transferring the anti-infective oxidant into a wall of the medical device. One embodiment includes the step of exposing a medical device that is at least in part within a patient to the anti-infective oxidant. Another embodiment includes the steps of exposing a medical device to an aqueous solution which produces the anti-infective oxidant and transferring a sufficient amount of the anti-infective oxidant into the medical device wall to provide the medical device with anti-infective activity. Also provided is an oxidant releasing member that has anti-infective oxidant releasably contained therein and that is configured to be disposed adjacent to the medical device. Exemplary devices include catheters such as venous, arterial, and urinary catheters, generally containing an elongated catheter shaft having a lumen extending therein, and optionally having a balloon on the shaft in fluid communication with the catheter lumen.

41 Claims, 14 Drawing Sheets

OTHER PUBLICATIONS

Gristina, "Biomaterial–Centered Infection: Microbial Adhesion Versus Tissue Integration", *Science*, 237, 1588–1595, (1987).

Gupta et al., "Increasing Prevalence of Antimicrobial Resistance Among Uropathogens Causing Acute Uncomplicated Cystitus in Women", *JAMA*, 281 (8), 736–738, (1999).

Houang et al., "Absence of Bacterial Resistance to Providone Iodine", *J. Clin. Path.*, 29, 752–755, (1976).

Jansen et al., "In–vitro Efficacy of a Central Venous Catheter Complexed with Iodine to Prevent Bacterial Colonization", *J. Antimicrobial Chemotherapy*, 30, 135–139, (1992).

LeVeen et al., "The Mythology of Povidone–Iodine and the Development of Self–Sterilizing Plastics", *Gynecology & Obstetrics*, 176, 183–190, (1993).

MacLellan, "Foreword", *Dermatology*, 195 (suppl. 2), 1–2, (1997).

Morain et al., "Iodinated Silicone–An Antibacterial Alloplastic Material", *Plastic and Reconstructive Surgery* 59 (2), 216–222, (1977).

Rodeheaver et al., "Pharmacokinetics of a New Skin Wound Cleanser", *American J. of Surgery*, 132, 67–74, (1976).

Shikani et al., "Polymer–Iodine Inactivation of the Human Immunodeficiency Virus", *J. of the American College of Surgeons*, 183, 195–200, (1996).

Tyagi et al., "Preparation and Antibacterial Evaluation of Urinary Balloon Catheter", Center for Biomedical Engineering, Indian Institute of Technology, New Delhi, India, paper # 97–040, (1997).

Zhang et al., "Antiinfective Coatings For Indwelling Medical Devices", *Medical Plastics and Biomaterials*, MPB Archive, Nov. 97, (1997).

Abstract of Kristinsson et al., *J. Biomater. Appl.*, 5(3), 173–184 (1991).

Derwent# JP 59228847 A: for Japanese Patent Application No. JP 83104573, "Moulded article having physiologically active substance fixed onto it–comprises moulding copolymer of monomer having acid anhydride radical with olefin, chlorinated olefin, vinyl ester and vinyl–ether of diene".

* cited by examiner

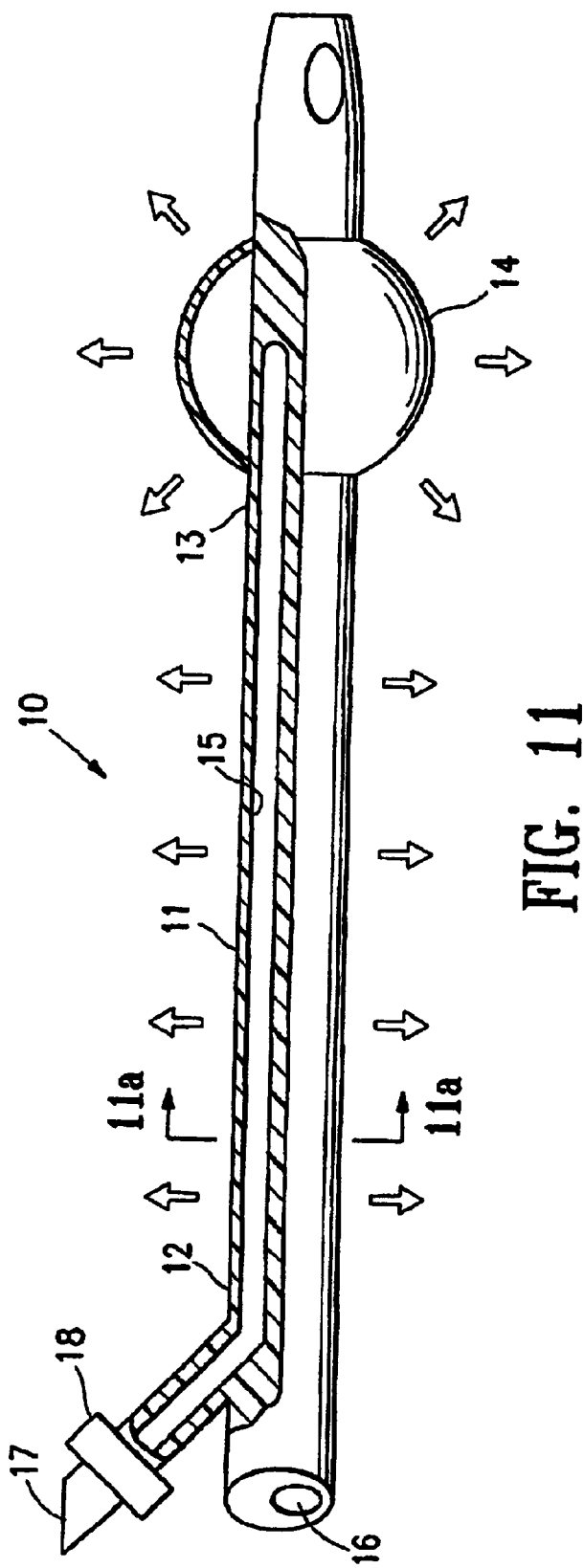
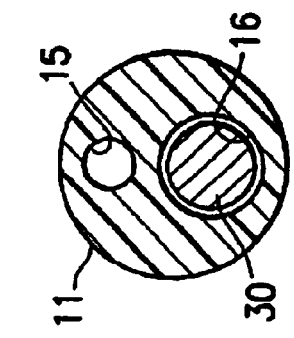
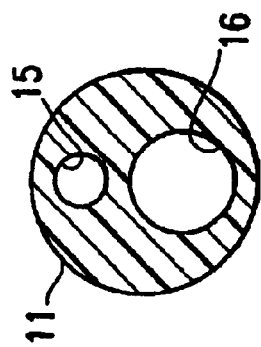
FIG. 11
FIG. 11a
FIG. 11b

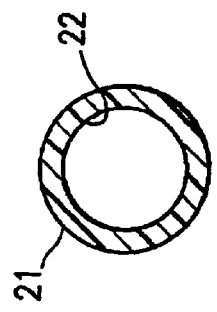
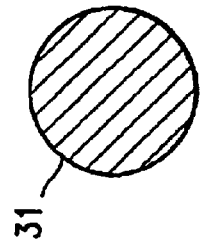
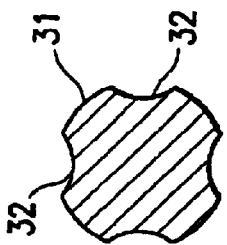
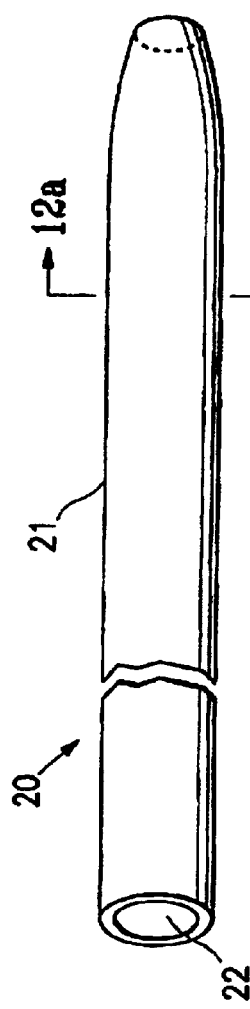
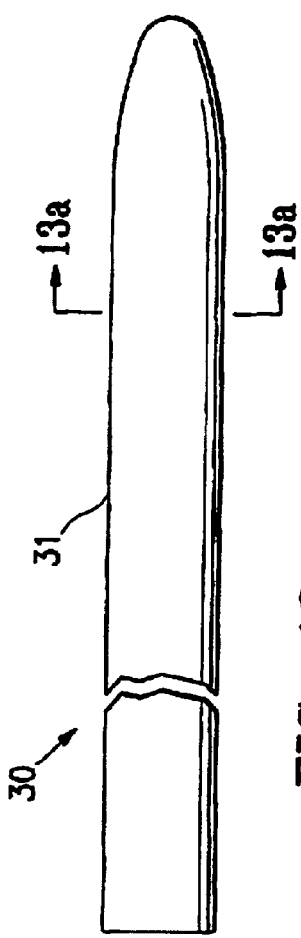

METHODS AND DEVICES FOR PROVIDING ANTI-INFECTIVE ACTIVITY TO A MEDICAL DEVICE

CROSS REFERENCE TO RELATED APPLICATIONS

This application claims the benefit under 35 USC 119(e) of Provisional Application Nos. 60/137,654, filed on Jun. 4, 1999, and 60/165,394, filed Nov. 12, 1999. These applications and other documents referred to elsewhere in the specification of this application are incorporated herein by reference in their entireties.

FIELD OF THE INVENTION

The invention is directed to methods and devices for providing anti-infective activity to a medical device, and more particularly to methods and devices for transferring anti-infective activity through in-situ presentation of formulations which generate anti-infective oxidant such as elemental iodine and allow for its transfer to the polymer base of urinary, venous, and other lumen indwelling medical devices, conferring to such devices prophylactic and therapeutic treatment of implant-linked infections.

REFERENCES

U.S. Patents:
U.S. Pat. No. 4,278,548 Bettinger et al. (1981) Control of biological growth in reverse osmosis permeators.
U.S. Pat. No. 4,312,833 Clough et al. (1982) Sterilizing hydrophilic contact lenses.
U.S. Pat. No. 4,476,108 Kessler et al. (1984) Bactericidal method.
U.S. Pat. No. 4,576,817 Montgomery and Pellico (1986) Enzymatic bandages and pads.
U.S. Pat. No. 4,937,072 Kessler et al. (1990) In situ sporicidal disinfectant
U.S. Pat. No. 5,227,161 Kessler (1993) Method to clean and disinfect pathogens on the epidermis by applying a composition containing peroxidase, iodide compound and surfactant
U.S. Pat. No. 5,232,914 Fellman (1993) Solid, storage-stable, germicidal. Pre-iodine composition.
U.S. Pat. No. 5,370,815 Kessler (1994) Viscous epidermal cleaner and disinfectant.
U.S. Pat. No. 5,419,902 Kessler (1995) Method for inactivating pathogens.
U.S. Pat. No. 5,462,713 Schiltzer et al. (1995) Double redox system for disinfecting contact lenses.
U.S. Pat. No. 5,607,681 Galley et al. (1997) Anti-microbial compositions.
U.S. Pat. No. 5,629,024 Kessler et al. (1997) Method of forming an iodine based germicide composition
U.S. Pat. No. 5,772,971 Murphy et al. (1998) Iodine-based microbial decontamination system.
Other Relevant Articles:
Barabas, E. S. and Brittain, H. G. (1998). Povidone-Iodine in Analytical Profiles of Drug Substances and Excipients (ed., Brittain, H. G.) Vol. 25, AP, San Diego, pp. 341–462.
Birnbaum, L. M., Hopp, D. D. and Mertens, B. F. (1982) The Role of Iodine-Releasing Silicone Implants in Prevention of Spherical Contractures in Mice. Plastic & Reconstructive Surgery 69 (6): 956–959.
Caufield, P. W. and Wannemuehler, Y. M. (1982) In vitro susceptibility of streptococcus mutans 6715 to iodine and sodium fluoride, single and in combination, at various pH values. Antimicrob. Agents Chemother. 22 (1): 115–9.
Conn, H. and Langer, R. (1981) Iodine disinfection of hydrophilic contact lenses. Ann. Ophthalmol. 13 (3): 361–4.
Gordon, J. (1993) Opening address, Closing remarks, and articles therein—Second Asian Pacific Congress on Antisepsis (Hong Kong) in Postgrad Med J 69 (suppl. 3), S1–S134.
Gristina, A. G. (1987) Biomaterial-Centered Infection: Microbial Adhesion Versus Tissue Integration. Science 237: 1588–1595.
Gupta, K., Scholes, D. and Stamm, W. E. (1999) Increasing Prevalence of Antimicrobial Resistance Among Uropathogens Causing Acute Uncomplicated Cystitis in Women. JAMA 281 (8): 736–738.
Houang, E. T., Gilmore, O. J., Reid, C. and Shaw, E. J. (1976) Absence of bacterial resistance to povidone iodine. J. Clin. Pathol. 29 (8): 752–5.
Jansen, B. et al. (1992) In-vitro efficacy of a central venous catheter complexed with iodine to prevent bacterial colonization. J. Antimicrobial Chemotherapy 30: 135–139.
Kristinsson, K. G. et al. (1991) Antimicrobial activity of polymers coated with iodine-complexed polyvinylpyrrolidone. J. Biomaterials Applications 5: 173–184.
LeVeen, H. H. et al. (1993) The mythology of povidone-iodine and the development of self-sterilizing plastics. Gynecology & Obstetrics 176: 183–190.
MacLellan, D. G. (1997) Foreword; Ermini, M. (1997) Current Povidone-Iodine Research: A Summary of the Papers Presented; see also articles therein—Third Asian Pacific Congress on Antisepsis (Sidney) in Dermatology 195 (suppl. 2), S1–S120 (and abstracts S121–S159).
Morain, W. D. and Vistnes, L. M. (1977) Iodinated Silicone—An Antibacterial Alloplastic Material. Plastic & Reconstructive Surgery 59 (2): 216–22.
Rodeheaver, G., Turnbull, V., Edgerton, M. T., Kurtz, L. and Edlich, R. F. (1976) Pharmacokinetics of a new skin wound cleanser. Amer. J. Surg. 132 (1): 67–74.
Shikani, A. H. et al. (1996) Polymer-iodine Inactivation of the Human Immunodeficiency Virus. J. Amer. College of Surgeons 183: 195–200.
Tyagi, M. and Singh, H. (1997) Preparation and antibacterial evaluation of urinary balloon catheter. Biomedical Sciences Instrumentation 33: 240–45.
Zhang, X., Whitbourne, R. and Richmond, R. D. (1997) Anti-infective Coatings for Indwelling Medical Devices. Medical Plastics and Biomaterials, November/December Issue, pp. 16–24.

The disclosure of these and other references listed in the specification are hereby incorporated herein by reference in their entireties.

BACKGROUND OF THE INVENTION

Introduction of medical devices implanted into the body can lead to serious nosocomial infections. Implanted medical devices (e.g., venous and arterial catheters, neurological prostheses, wound drains, urinary "Foley" catheters, peritoneal catheters, and other lumenal indwelling devices), while sterilized and carefully packaged to guard against introduction of pathogens during implantation, pose a risk during insertion, and subsequently. During insertion bacteria can be picked up from the skin and carried into the insertion site where bacterial colonization may ensue. In the case of urinary and venous catheters, especially those used long term, there is a significant threat of microbial growth along the exterior surface of the catheter. This can lead to chronic urinary tract infections (CUTI), or septicemia in the case of venous and arterial catheters, thrombolytic emboli caused with infections introduced by the catheter, and other life-threatening complications, especially among the elderly. Methods aimed at circumventing this problem have included irrigating the implant site with antibiotic, applying various antibiotic ointments or antibiotic impregnated sponges near the exterior opening by which infection most likely occurs, impregnating the polymer base coating the implant device with antibiotics, or silver, either as a heavy metal or in combination with antibiotics, or treatment of patients systemically with antibiotics. Despite the foregoing attempts at preventing infections associated with the implantation of catheters and lumenal indwelling devices in various body cavities, these methods of preventing and treating infections have not proven satisfactory.

For example, the long term use, and misuse, of antibiotics often results in the selection of antibiotic resistant strains. Hence, in general, systemic antibiotic therapy is ill advised and ineffective in warding off CUTI, for example. The secondary side effects of systemic antibiotic treatments can also pose a serious risk to many patients. Furthermore, in many implant sites, the formation of fibrous tissue around the implant site reduces the supply of blood to the implant cavity thereby precluding systemic antibiotic treatment of the critical space between the implant and capsular endothelial wall. In the case of a urinary catheter (e.g., Foley catheter), antibiotics injected as a coating in the urinary canal may be washed out during drainage through leakage of some urine along the urinary tract outside the catheter, or resorbed before they can achieve sufficient levels to effectively kill bacteria growing within localized regions of the urinary tract.

It can be appreciated from the foregoing problems that there is a pressing need for the development of better methods of preventing and treating infections caused with catheter insertions into body cavities, particularly for the development of methods and devices which circumvent the problem of selecting out antibiotic resistant organisms. The problem is particularly acute since it is known that when catheters, and other indwelling lumenal devices, are inserted into body cavities such as the urinary tract, venous or arterial vessels, a biofilm forms rapidly on the walls of the implant device. Bacteria then propagate free from attack by the body's own phagocytic defense system, and also free from systemic antibiotic treatments (Gristina, A. G., Science 237: 1588–1595 (1987); Zhang, X. et al., Medical Plastics and Biomaterials, November 1997, pp. 16–24).

Free elemental iodine is attractive as an anti-infective agent. There are no known organisms which have developed resistance against its oxidizing activity in attacking critical sulfhydryl groups, and other functional groups in proteins, essential for bacterial survival (Second Asian Pacific Congress on Antisepsis in Postgrad. Med. J. 69 (suppl. 3), 1993: S1–S134; Third Asian Pacific Congress on Antisepsis in Dermatology 195 (suppl. 2), 1997: S1–S120). A few parts per million (ppm) in solution is sufficient to kill bacteria and viruses (LeVeen et al. (1993) Gynecology & Obstetrics 176: 183–190; Barabas, E. S. and Brittain, H. G. (1998) in Analytical Profiles of Drug Substances and Excipients (ed., Brittain, H. G.) Vol. 25, AP, San Diego, pp. 341–462). On the other hand, because of its high degree of diffusion through water, air and lipids, and its reactivity as an oxidizing agent, elemental iodine is difficult to handle in a clinical setting.

Methods of stabilizing iodine in solution illustrated by the formulation, Povidone-iodine, for example, are well known to those in the art. This formulation has been tried without satisfactory success in conferring to catheters anti-infective properties. Povidone-iodine washes free of devices as a coating, and is consequently present an insufficient duration to significantly reduce the incidence of infections brought on following implantation, particularly in complex biological media Jansen et al. (J. Antimicrobial Chemotherapy 30: 135–139 (1992)), and Kristinsson et al. (J. Biomaterials Applications 5: 173–184 (1991)), sought to confer to catheters anti-infective activity by preloading the lumen with iodine complexed with polyvinylpyrrolidone (PVP). While they were able to demonstrate weak anti-infective activity in aqueous buffered solutions, this strategy proved unsatisfactory in complex media Jansen reported that the activity conferred by this technique lasted for less than 3 hours in serum. Indeed, Jansen sought to preload PVP coated catheters with Lugol's solution, a concentrated mixture of inorganic iodine and iodide, in an attempt to enhance the anti-infective activity of the iodine transferred to the catheter lumen. As noted below, and in example 8 illustrating the invention described herein, the use of iodophor complexing agents such as PVP, designed to sequester elemental iodine, works against, rather than promotes, conference of anti-infective activity to catheters. This can be appreciated since iodophors, in binding iodine, compete for iodine, decreasing its rate of egress across the polymer base of the catheter, thus ameliorating the effectiveness of iodine in conferring to catheters anti-infective activity.

Povidone-iodine as it is commercially formulated with a total iodine content of 10,000 ppm also introduces a high iodine exposure level to the patient of which only about 1 ppm is free iodine, the form necessary to affect microbial killing. PVP, the binding agent used in trapping iodine in aqueous solutions in a bound form, is also problematic in retarding wound-healing (LeVeen et al. (1993) Gynecology & Obstetrics 176: 183–190). The short-lived retentions of Povidone-iodine coatings on implant devices, the fact that binding agents such as PVP aggravate wound-healing, and the fact that the free form of iodine in Povidone-iodine at 1 ppm is below the essential ~2 ppm level of free iodine required for efficient microbial killing, points out the need for a better method of presenting iodine as an anti-infective agent to catheters, and other indwelling implant devices (e.g., wound drains).

Morain and Vistnes (Plastic & Reconstructive Surgery 59: 216–222 (1977)) sought to impregnate silicone discs with elemental iodine by soaking discs in 95% ethanolic solutions in which crystalline iodine had been dissolved, and then tested the discs for anti-infective activity. While they were able to demonstrate the release of anti-infective activity in their iodine impregnated disc samples, they concluded that the use of iodine was "contraindicated" because of concern that it would add to the vinyl group of polymethylvinylsiloxane in the formulations they used, potentially altering "the substance sufficiently that an entirely new set of physiochemical properties might result." It is also apparent that the method of impregnating an implant using crystalline iodine and an alcoholic solution is impractical in a clinical setting. Iodine crystals in combination with alcohol can cause severe chemical burns if put into direct contact with tissues, it is difficult to control dosing of crystalline iodine in a reliable fashion, and messy working with mixtures of crystalline iodine and alcohol. Thus the practical obstacles of preparing impregnated anti-infective implants using this technology pose serious logistical problems in the handling and release of iodine.

Birnbaum et al. (Plastic & Reconstructive Surgery 69: 956–959 (1982)) sought to confer to silicone breast implants anti-infective activity by injecting Povidone-iodine solutions into the internal cavity of the implants in studying prevention of spherical contractures believed to be caused by inflammation, but found comparable fibrosis, collagen deposition and inflammation to that of control animals implanted with silicone implants lacking anti-infective activity. Birbau et al. taught that in their formulation "the effects of iodine are limited to a proscribed period of time, following which all inhibitory activity is lost." They concluded that ". . . Bacteria arriving subsequent to this period of activity would not be inhibited. Fibrosis and late scar contracture might then ensue . . ." thus teaching away from the use of delivering free iodine into silicone polymer implants.

LeVeen and LeVeen (U.S. Pat. No. 5,156,164) claimed to have conferred bactericidal activity to a contraceptive sponge by impregnating the polyurethane polymer base comprising the sponge with an aqueous solution of free iodine made up in Lugol's solution. More recently, Shikani and Domb (U.S. Pat. Nos. 5,695,458; 5,762,638) described the fabrication of iodine impregnated polymer coatings of varying thickness prepared by dissolving elemental iodine into organic solvents which also contained organic polymers which were then layered and coated by dipping and drying steps over medical devices including blood handling collection bags, tubes, catheters, and the like. This technology involves multiple layering of iodine impregnated polymers, the spacing of additional layers of polymer lacking iodine dissolved in the organic solvents, and varying such steps aimed at retarding and managing the egress rates of free iodine from the polymer base to provide for a controlled anti-infective activity. Tyagi and Singh (Biomedical Sciences Instrumentation 33: 240–45 (1997)) in a similar fashion sought to confer to latex Foley urinary balloon catheters anti-infective activity by dipping the outer external surfaces of the latex balloon in toluene solutions comprising a mixture of elemental iodine and latex, and then drying and storing catheters treated in this manner at low temperature in polythene bags prior to use, however. Neither the polyurethane nor latex methods are amenable to on site delivery of anti-infective activity to an existing catheter or implant device at the bedside, or in the surgical suite. The use of organic solvents, drying times and multiple dipping steps make these methods impractical in a clinical setting in conferring anti-infective activity to the implant device.

The latter techniques of entrapping elemental iodine within a polymer base as taught by LeVeen and LeVeen, Shikani and Domb, and Tyagi and Singh, rely, in general, on starting with free elemental iodine dissolved within a solvent system, and trapping it within a polymer base, a process wrought with technical difficulties. The layering and drying steps used in the art taught by Shikani and Domb, and Tyagi and Singh, moreover, is costly and time consuming. In addition, none of the methods starting with free elemental iodine address the problem of how to ensure a long shelf life for iodine entrapped within the polymer base of the implant device. Once the device is fabricated and loaded with iodine, it can be appreciated by those knowledgeable in the art that iodine will begin to diffuse into the air because of the inherent chemical properties of iodine to disperse free of its initial site of deposition. Furthermore, the high degree of reactivity of free iodine is a drawback to these methods. It can be anticipated, for example, that iodine will react and become depleted from the device in encountering varying reducing compounds coming into contact with the device. Such compounds capable of depleting the iodine entrapped within the device may be in the form of gases, liquids or solids including the wrapping materials in which the devices are stored. In addition to these limitations, in the art taught by Shikani and Domb, and Tyagi and Singh, the layering of varying polymer layers atop one another using organic solvents in which iodine is dissolved is limited to polymers which are compatible with one another in forming strong and uniform adhesive bonds, and which will not swell or alter shape when wetted and presented to a biological site of treatment. This is contrary to the properties of many medical grade polymers used in medical devices that have a tendency to swell and distort in shape once placed within the body. Polymer swelling and distortion is unacceptable in the art taught by Shikani and Domb since the latter phenomenon results in rupturing of the adhesive bonds between the iodine coated layers of the implant device and loss of control in the release rates of free iodine egressing from the device.

Therefore, there remains a need in the art to mitigate the risk of infection from such medical devices.

SUMMARY

The invention is directed to methods of providing anti-infective activity to a medical device generally comprising exposing the medical device to an anti-infective oxidant and transferring the anti-infective oxidant into a wall of the medical device. One embodiment comprises exposing a medical device which is at least in part within a patient to the anti-infective oxidant The phrase within a patient should be understood to mean a device which is disposed in a natural body lumen such as an oral or vaginal cavity, as well as a device disposed in the body via a surgical incision therein. Additionally, the term "patient" should be understood to include humans as well as animals. Another embodiment comprises exposing a medical device to an aqueous solution which produces the anti-infective oxidant and transferring a sufficient amount of the anti-infective oxidant into the medical device wall to provide the medical device with anti-infective activity. Another aspect of the invention is directed to an oxidant releasing member which has the anti-infective oxidant releasably contained therein and which is configured to be disposed adjacent to the medical device. Presently preferred medical devices usefull in the method of the invention include catheters such as venous, arterial, and urinary catheters, generally comprising an elongated catheter shaft having a lumen extending therein, and optionally having a balloon on the shaft in fluid communication with the catheter lumen.

The medical device can be exposed to the anti-infective oxidant by a variety of suitable methods. In one embodiment, the medical device is exposed to a formulation which generates the anti-infective oxidant For example, the formulation can be delivered into a lumen of the device or into the interior of a balloon of the device, or the device can be at least in part submerged within the formulation. The formulation can be delivered into the lumen of the medical device using a tubular delivery member inserted into the medical device lumen or by attaching a source of the formulation to a port, such as the port in a side arm adapter, on the proximal end of the medical device. A viscosity increasing compound such as a hydrogel, such as a carbopol, may be added to the oxidant generating formulation to inhibit the expulsion of the formulation from the medical device lumen. In an alternative embodiment, the oxidant is transferred into a wall of the medical device from an oxidant releasing member having the anti-infective oxidant releasably contained therein. The oxidant releasing member is preferably formed of a polymer, and has a dispersion of the oxidant within the polymer. The oxidant releasing member may be provided with the oxidant by a variety of suitable methods. For example, the oxidant releasing member can be exposed to a formulation which generates the oxidant, so that the oxidant diffuses into the polymeric wall of the oxidant releasing member. Alternatively, the oxidant releasing member can be formed of a polymer having a solid-phase dispersion of oxidant producing compounds therein which require a component such as water to be exposed to the oxidant producing compounds to produce the oxidant when desired. A presently preferred material of the oxidant releasing member is a hydrophobic polymer, such as a polyethylene, however, a variety of suitable materials may be used depending on the oxidant type and concentration, and the medical device used. In a presently preferred embodiment, the oxidant releasing member has an elongated body configured to be slidably inserted into a lumen of the medical device. However, the oxidant releasing member may, alternatively, be configured to be disposed around at least a section of the medical device. The oxidant releasing member may have a variety of suitable shapes including rods, tubes, or the like. In one embodiment, the oxidant releasing member is a rod having at least one channel on an outer surface of the rod configured to allow fluid flow therein. In certain types of catheters where liquids cannot be safely injected directly into the lumenal space, as in the case of a certain venous or arterial catheters, the insertion of an oxidant releasing member into the lumen of the catheter is the preferred method of exposing the medical device to the anti-infective oxidant. Alternatively, in catheters such as urinary catheters, the oxidant generating formulations can typically be introduced into the catheter lumen.

After a short interval following exposure of the medical device to the anti-infective oxidant, as for example by introduction of the oxidant generating formulation or oxidant-loaded rod into the lumenal space of the device, sufficient to allow for transfer of the oxidant to the walls of the medical device, the oxidant generating formulation or the rod can be removed, having deposited its intended load of anti-infective oxidant to the medical device. Thereafter, oxidant diffuses to the external walls of the medical device, conferring to it anti-infective activity. In a presently preferred embodiment, a single exposure to the anti-infective oxidant is required to provide the medical device with anti-infective activity for a given period of time, unlike prior art methods requiring multiple exposures. The medical device is exposed to the anti-infective oxidant typically for about 1 to about 30 minutes to transfer the oxidant to the medical device. The oxidant generating formulation introduced into the medical device lumen or exposed to the oxidant releasing member produces sufficient amounts of anti-infective oxidant to transfer about 2 to about 300 ppm, preferably about 2 to about 10 ppm of anti-infective oxidant into a wall of the medical device. The oxidant generating formulation produces about 0.1 to about 300 ppm, preferably about 2 to about 10 ppm of anti-infective oxidant, depending on the oxidant used.

The anti-infective oxidant has microbicidal and virucidal activity due to its oxidative activity. Suitable anti-infective oxidants include elemental iodine (also called free iodine), hypohalites, haloamines, thiocyanogen, and hypothiocyanite. The anti-infective oxidants are produced by the oxidant generating formulations by the oxidation, reduction, or hydrolysis of the oxidant producing component.

In the case of elemental iodine, the oxidant producing component in the oxidant generating formulation is an iodine-containing salt which is oxidized or reduced, to produce elemental iodine. A source of protons is required to drive the oxidation or reduction of iodine-containing salt to elemental iodine. Iodine-containing salts suitable for use in the invention include iodides, which oxidize to elemental iodine, and iodates, which reduce to elemental iodine. Suitable iodides include any of the iodides of alkali and alkaline earth metals, such as sodium iodide, potassium iodide, calcium iodide, and barium iodide. Suitable iodates include iodates of alkali metals such as sodium iodate, potassium iodate, and iodine pentoxide. In the case of iodates, the iodate may act as both a source of iodide, and an oxidizing agent which oxidizes iodide to elemental iodine.

This invention takes advantage of the chemical properties of iodine to diffuse freely through hydrophobic and hydrophilic phases and exploits this property of iodine in moving it to desired sites for egress to the exterior surfaces of lumenal implant devices where anti-infective activity is needed to prophylactically prevent, and to treat, infections linked with implantation of the lumenal device. Moreover, oxidant generating formulations used in the method of the invention provide for rapid formation of elemental iodine. The oxidant generating formulations preferably include a suitable proton source along with precursors required for the generation of elemental iodine, to ensure rapid formation of elemental iodine, and consequently the rapid uptake of elemental iodine by the medical device or the oxidant releasing member. The oxidant generating formulation produces at least about 0.1 ppm of elemental iodine, and preferably about 2 ppm to about 300 ppm of elemental iodine, and most preferably about 5 ppm to about 10 ppm elemental iodine per treatment, so that about 2 ppm to about 300 ppm of the elemental iodine per treatment, or about 2 micrograms of elemental iodine per day, preferably not more than 1500 micrograms of elemental iodine per day diffuses from the medical device to the patient to provide anti-infective activity to the medical device.

In the case of hypohalite as the anti-infective oxidant, the oxidant producing component comprises a halide-containing compound oxidized by an oxidizing agent to produce the hypohalite. Similarly, a thiocyanogen or hypothiocyanite anti-infective oxidant can be produced by the oxidation of a thiocyanate.

A variety of suitable oxidizing agents may be used to oxidize the oxidant producing component, including iodine oxide salts, peracids, and substrate oxidoreducatases. Suitable iodine oxide salts include alkai or alkaline earth metal iodates such as potassium iodate, sodium iodate or calcium iodates, and iodine pentoxide. Suitable peracids include perborates and organic peroxyacids.

A variety of suitable reducing agents may be used to reduce the oxidant producing component. For example, where the oxidant producing component is an iodate, any iodate oxidizable substrate such as ascorbate, thiols, and organic aldehydes may provide the reducing equivalents to reduce iodate to elemental iodine.

A variety of suitable proton producing agents may be used including an anhydride which upon exposure to water spontaneously hydrolyzes to an acidic product, or an enzyme acting on a substrate which catalyzes formation of an acid product In a presently preferred embodiment, the proton producing agent is selected from the group consisting of iodine pentoxide, an organic or inorganic acid, and enzyme oxidase such as glucose oxidase, and an anhydride such as succinic anhydride, maleic anhydride, succinyl maleic anhydride and acetic anhydride.

Although discussed primarily in terms of an elemental iodine anti-infective oxidant, it should be understood that the various embodiments discussed herein may involve the use of alternative anti-infective oxidants. Thus, for example, alternative oxidants which can be caused hypoiodite (OI⁻), and hypobromite (OBr⁺); haloamines including chloramines, iodamines, and bromamines which are the oxidizing products formed through reaction of hypohalites with primary and secondary amines such as taurine chloramine formed by introduction of taurine to hypochlorite; thiocyanogen ($(SCN)_2$); and hypothiocyanite ($OSCN^+$).

The method of the invention provides improved anti-infective activity to medical devices, due to the anti-infective oxidant which is formed in solution rapidly and in sufficient quantity to deposit controllable, desired concentrations of the oxidant onto the lumenal walls of the medical device, or loading rod, whence transfer across the polymer wall ensues. The ability to exploit chemical formation of free iodine de novo, and positioning and transfer of elemental iodine using this chemistry within the lumenal cavity at a specific site for the treatment and prevention of infections, is of great advantage because it allows this technology to be used on existing lumenal implant devices such as urinary, venous and arterial catheters, wound drains, and other indwelling lumenal devices, without the expense and retooling necessary in manufacturing anti-infective activity into a device as it is produced by the manufacturer. Furthermore, this technology allows clinicians and users of this art to tailor the frequency of treatment to the needs of the patient in preventing, or treating, an infection, and thus this technology offers great flexibility in its application in the clinical setting. These and other advantages of the invention will become more apparent from the following detailed description and accompanying figures.

BRIEF DESCRIPTION OF THE DRAWINGS

FIG. 11 is a schematic illustrating loading of ICAT iodine generating formulations into the inflatable balloon of a Foley urinary catheter by placing ICAT solution contained in a Luer-lock syringe (not shown) into the entry port of the valve at the proximal end of the catheter. Compression of the syringe expresses ICAT solution through the internal cannular lumen built into the wall of the Foley catheter which communicates with the balloon, and allows ICAT solution to enter and inflate the balloon. The central lumen allows for urine to pass freely from the bladder via the bladder drain through the catheter and into a urine waste container (not id shown). The light arrows perpendicular to the plane of the catheter walls depict egress of free iodine across the catheter wall and to the external surface of the catheter, conferring anti-infective activity to the ICAT-loaded catheter.

FIG. 11a illustrates a transverse cross-sectional view of the catheter shown in FIG. 11, taken along lines 11a—11a.

FIG. 11b illustrates a transverse cross-sectional view of a catheter having an oxidant releasing member in a lumen of the catheter.

FIG. 12 is an elevational view of tubular delivery member which embodies features of the invention.

FIG. 12a illustrates a transverse cross-sectional view of the tubular delivery member shown in FIG. 12, taken along lines 12a—12a.

FIG. 13 is an elevational view of an oxidant releasing member which embodies features of the invention.

FIG. 13a illustrates a transverse cross-sectional view of the oxidant releasing member shown in FIG. 13, taken along lines 13a—13a.

FIG. 14 illustrates a transverse cross-sectional view of an alternative embodiment of the oxidant releasing member, having grooves in an outer surface of the oxidant releasing member.

DETAILED DESCRIPTION OF THE INVENTION

Figure 1:
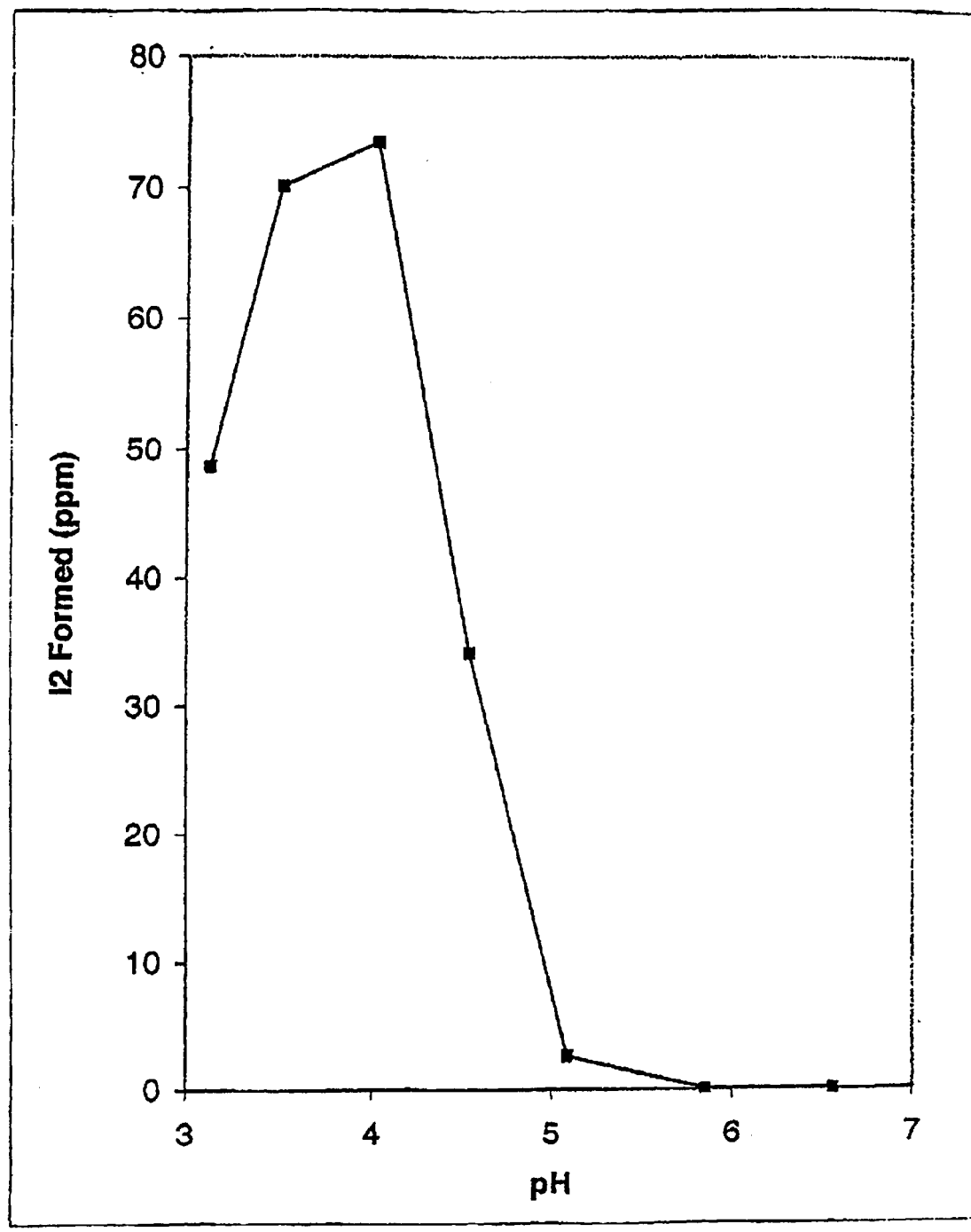
FIG. 1 shows the effect of varying the pH of buffered citrate solutions (50 mM) on the rate of free elemental iodine formation using potassium iodide and sodium iodate as precursors. The optimal pH for iodine formation is approximately 4.5.

Overview of the Device and Formulation Chemistry

In a presently preferred embodiment, the anti-infective oxidant is elemental iodine. The de novo generation of free elemental iodine from precursor inorganic iodide provides the basis for producing free iodine on demand, as needed, in allowing for transient presentation and transfer of iodine to lumenal catheter implant devices. Varying methods and formulations for its production have been described in prior art (U.S. Pat. Nos. 4,278,548, 4,312,833, 4,476,108, 5,232,914, 5,607,681, 5,648,075, 5,849,241). These methods have in common the presentation of inorganic iodide, an oxidant (either enzymatic or inorganic), a proton source and water as a solvating agent in combination to affect formation of free elemental iodine through oxidation and conversion of iodide into iodine in accordance with the following general equation:

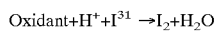

$$\text{Oxidant} + H^+ + I^{31} \rightarrow I_2 + H_2O$$

Depending upon the oxidant used, other byproducts of the reaction may arise (vis., gluconate in the case of glucose oxidase wherein the proton generated in the formation of gluconic acid, and hydrogen peroxide formed with consumption of molecular oxygen, are converted to water concomitant with iodine formation). In the present invention, the precise method of forming free elemental iodine de novo staring with inorganic iodide is not critical as long as excess iodine is formed in solution rapidly and in sufficient quantity to deposit onto the lumenal walls of the implant device, or loading rod, whence transfer across the polymer wall ensues. The other key elements in the present invention involve devices for positioning of the chemistry within the implant device at appropriate sites required for conferring anti-infective activity to the implant device, and exploitation of the properties of the lumenal space in ensuring appropriate dispersion of free iodine to the desire sites of treatment.

The principle of transiently loading lumenal implant devices with anti-infective free iodine exploits the propensity of free iodine to diffuse freely through hydrophilic and hydrophobic polymers, and thus to disperse to the exterior wall of the implant device where anti-infective activity is sought in prophylactically preventing the establishment of an infection between the exterior walls of the implant device, and the biofilm formed on the surface of the device. Similarly, where an infection has become established in an existing implant body cavity, free iodine can be delivered to the site using this technology through movement of iodine generated de novo across the walls of the implant device to the localized site of infection adjacent to the implant device. To achieve bacterial killing, the free iodine level egressing from the device should preferably attain a level of not less than 2 ppm nor exceed about 300 ppm within the body fluid to be treated. Levels in excess of 300 ppm or unnecessary and may lead to crystallization of free iodine from the body fluid resulting in undesirable concentrations of iodine within the treatment site.

Delivery of Free Elemental Iodine Anti-Infective Activity to the Implant Device For delivery and positioning of the chemistry within the lumenal space of the implant device, three general techniques have been developed. The first is to use a "blind"

lumen (a dead-end lumen without communication to body fluids), or a balloon cannular entry port fabricated into the implant device as the means for delivery of free iodine to the implant device. An example of this type of delivery vehicle entails use of inflatable balloons built into catheters such as a Foley catheter for retention of the inserted device within the urethral canal and anchored by inflation of the balloon at the base of the bladder. In this design, a separate lumen is designed into the catheter leading to an inflatable balloon with a septum lock in which sterile water is ordinarily injected in expanding the balloon once it has been inserted with its tip and deflated balloon end penetrating into the bladder from the urethral canal. Such devices are common in catheter devices used to anchor, or secure, catheters against the walls of a vessel, and are familiar to those working in this art In the present invention, the lumen used to inflate the balloon, as well as the internal reservoir of the balloon, can be used as the site for delivering iodine generating chemistry by substituting an appropriate iodine generating formulation (see below) in place of sterile water as the inflating agent for the balloon. The frequency of dosing and loading the catheter with anti-infective iodine can be made as desired by replacing the fluid injected through the lumen to the balloon reservoir with fresh solutions of iodine generating formulation. Iodine generated within this reservoir, and within the lumen leading to the balloon, disperses readily to the walls of the implant device, and egresses to the external walls of the device, thus lending to the device anti-infective properties. A similar cannular loading port and balloon to allow for loading of free iodine, generated de novo in the loading solution, can be built into a venous or arterial catheter to confer to the latter anti-infective activity. FIG. 11 illustrates a urinary catheter 10 having a catheter shaft 11 with a proximal end 12, a distal end 13 and an inflatable balloon 14 on a distal section of the shaft. The balloon has an interior in fluid communication with inflation lumen 15 which extends within the catheter shaft 11. The catheter shaft also has a central drain lumen 16 which extends from a port on the proximal end of the catheter to a port on the distal end of the catheter, which, in use, is typically connected to a waste container for body fluids. A valve or connector 18 is on the proximal end of the catheter, and the inflation lumen 15 is in communication with port 17 on the proximal end of the catheter at the valve 18. FIG. 11a illustrates a transverse cross-sectional view of the catheter shown in FIG. 11, taken along lines 11a—11a. As discussed above, the oxidant generating formulation is introduced into the inflation lumen 15, central lumen 16, or the interior of balloon 14. FIG. 11b illustrates an oxidant releasing member 30 disposed within the central lumen 16 of the catheter 10 in accordance with the method of the invention. The oxidant releasing member could alternatively be introduced into the inflation lumen 15.

Where liquid formulation can be tolerated within the central lumen of the medical device, free iodine generated de novo can be delivered directly into the central lumen at a point distal from the proximal drain port as desired. In one embodiment, a tubular delivery member 20, as illustrated in FIG. 12, comprising a body 21 and a lumen 22 configured to deliver the fluid into the device lumen is used to deliver the formulation. FIG. 12a illustrates a transverse cross section of the tubular delivery member 20 shown in FIG. 12, taken along lines 12a—12a. The tubular delivery member 20 is preferably narrow bore, flexible tubing cut to the desired length, and fitted with a Luer lock over a syringe (not shown) loaded with the iodine generating formulation. The tubing 20 is typically inserted into the lumen 16 of the catheter through the drain site of the catheter so that the tubing slides as far as possible into the lumen, and allows for positioning of the end of the tubing used to deliver free iodine formed in the loading formulation at the point of application desired within the catheter. With expulsion of the syringe contents into the lumen, in a closed end lumen, fluid injected from the syringe flows backward from the dispensing tip toward the exit drain site since this is the route of least resistance. Hence, free iodine can be delivered from the loading tip of the tubular delivery member 20 inserted into the catheter lumen 16 back towards the drain site over any region of the catheter as desired. Following a brief interval of no more than a few seconds after dispersion of the free iodine generating solution, the tubular delivery member 20 may be withdrawn, leaving the loaded formulation to flush free of the lumen catheter through natural drainage of the lumen with body fluids. Alternatively, the formulation can be flushed or withdrawn by reinsertion of the tubular delivery member 20 back into the lumenal cavity of the catheter, and by injecting a wash solution of isotonic saline, or drawing back on the syringe plunger, depending upon the option chosen, following transfer of free iodine formed in the chemical formulation to the walls of the catheter.

The third embodiment for loading free elemental iodine into an indwelling catheter, or lumenal implant device, involves inserting an oxidant releasing member containing the anti-infective oxidant into the catheter lumen. In a presently preferred embodiment, the oxidant releasing member is a solid, flexible rod, fabricated to the length and diameter of the lumen device in which it is to be inserted, which is at least in part immersed into an iodine generating formulation made up and activated to form free elemental iodine just before insertion of the rod into the device. FIG. 13 illustrates an oxidant releasing member 30 which embodies features of the invention, having a body 31 configured to be slidably disposed in the medical device lumen. In the embodiments illustrated in FIGS. 12 and 13, the delivery and releasing members 20/30 have tapered distal ends to facilitate insertion within the device lumen. However, a variety of suitable configurations may be used, including distal ends which are not tapered. FIG. 13a illustrates a transverse cross section of the oxidant releasing member 30 shown in FIG. 13, taken along lines 13a—13a. FIG. 14 illustrates an alternative embodiment of the oxidant releasing member in which grooves 32 are provided on an outer surface of the body 31. The grooves are typically longitudinally disposed along the axis of the body 31 to allow fluid to flow through the lumen insert, or drain from the insert, with the rod in place during transfer of iodine to the walls of the implant device. The rod can be fabricated to serve as a plug, fitting snugly against the inner walls of the lumenal wall of the implant device during transfer of iodine anti-infective activity to the implant device. This third embodiment addresses transfer of anti-infective iodine activity to lumenal walls of implant devices such as venous or arterial catheters where direct injection of iodine generating fluid formulations into blood is unacceptable because of pH incompatibilities, the possibility of adverse reactions of components of the iodine generating formulation with constituents in blood, or the possibility of thrombolytic reactions induced with delivery of the formulation fluid directly into the blood stream. The solid rod serves as a solid-phase transporter of free iodine. In the case of a venous catheter, for example, the rod would displace blood from the catheter, yet upon removal, leave no residual fluid within the lumen space. Suitable materials for fabrication of the rod include, but are not restricted to, hydrophobic polymers such as polyethylene, Teflon, silicone, polystyrene, polypropylene, polyurethane, and/or polycarbonate. The critical feature is that the solid polymer is able to accept free iodine generated de novo from the iodine generating formulation in which the rod is immersed, and upon removal and insertion of the rod into the implant lumen, that free iodine taken up in the rod is then able to re-equilibrate and back-diffuse out of the rod and into the walls of the implant device whence anti-infective activity is conferred to the implant device.

While it should be appreciated that there is considerable latitude in the design of the rod insert with regard to its length and geometrical shape, preferably the rod insert should be of small enough diameter so that it slides smoothly through the lumen of the implant device without binding or grabbing too tightly against the walls of the inner lumenal wall precluding its easy insertion to the full insertion length intended in its positioning within the lumen. This restriction also dictates that it have sufficient stiffness, yet flexibility, so that it can be pushed into the lumen without hanging up on the walls of the lumen. Alternatively, it is desirable that the reservoir for holding free iodine is of practical volume so as to allow for a significant transfer of iodine to the walls of the implant device. In a practical application, the rod should occupy not less than about 5% nor more than about 90% of the total volume of the lumen space when inserted, with the preferred diameter approximately 80% of the inner lumenal wall diameter of the implant device. Furthermore, in the preferred embodiment, the ends of the rod should be rounded so as to allow it to slide freely along the inner lumenal wall of the implant without binding or catching.

In the case of the tubular delivery member designed for insertion and loading de novo generating iodine formulations directly into the central lumen of an implant device, the diameter of the loading lumen should most preferably be kept small relative to the diameter of the implant lumen to receive anti-infective iodine. In the loading cannula, its outer diameter should be not less than about 5% nor exceed by more than about 90% the diameter of the implant lumen, with the preferred diameter about 10% of the implant inner wall diameter. As in the case of the rod insert, the tubular delivery member should preferably have a rounded edge at its loading end to prevent binding and catching of the tubular delivery member on the inner lumenal walls of the medical device as it is inserted, and similarly it needs to have a flexibility and stiffness suitable so that it allows for easy insertion and sliding of the loading tip to the desired site within the medical device.

Formulation Used for Generating De Novo Free Elemental Iodine Anti-Infective Activity Although as noted in the overview there are several formulations for generating free elemental iodine, in the preferred embodiment sufficient inorganic iodide must be available, along with an oxidant and a proton source, to ensure production of free elemental iodine in excess of 300 ppm. In this manner, iodine generated de novo can be caused to quickly enter within the inner walls of the implant lumen, or onto the loading rod insert, thereby accelerating and improving the efficiency of transferring iodine to the implant device. In certain applications a hydrogel may be included in the formulation to increase the viscosity of the final formulation so that it does not readily flush out of the device with removal of the loading cannula used in depositing the formulation into the inner lumen of the indwelling device. While there are a variety of oxidants such as perborates, peroxy acids, enzyme oxidoreductases (vis., glucose oxidase, diamine oxidase, galactose oxidase, etc.) in combination with peroxidases (vis., horse radish peroxidase, lactoperoxidase, etc.) which may be used in combination with inorganic alkali salts of iodide to affect de novo formation of elemental iodine, in a preferred embodiment, the formulation for generating de novo free iodine can be made up as a two component solution in which the oxidants and inorganic iodide are kept separate from one another until mixing the two solutions together. Protons, or a proton generating source (for example, glucose oxidase), is also included in one of the two solutions, preferably with the oxidizing agent. In the case of using an enzyme such as glucose oxidase as the proton generating source, the substrate (vis., glucose) used to activate the reaction must therefore be provided in the alternate solution, or be present in the body fluid in which the device is inserted. Thereafter, the formation of de novo free iodine should ensue within no less than a few seconds, and preferably not more than about one hour, in conferring to the implant anti-infective activity. The desired endpoint is to achieve a presentation of free iodine at not less than about 2 ppm, nor more than about 300 ppm free iodine whether this level is generated rapidly, or over more extended intervals, sufficient to kill organisms attempting to colonize the implant device and surrounding tissue adjacent to the implant An example of a preferred de novo free iodine formulation, made up in Parts "A" and "B", is as follows:

Part A

From about 0.1 mM to not more than about 50 mM alkaline salt of iodine made up in sterile water, with the preferred salt made up as potassium iodide.

Part B

From about 0.1 mM to not more than about 50 mM iodate salt made up preferably as sodium or potassium iodate, preferably 20 mM, in from about 0.05 to 1% B. F. Goodrich Carbopol C971, C974 or Polycarbopol, adjusted with dilute base or acid as required, to a pH ranging from about 3.5 to about 6.0, preferably pH 4.5, in sterile water, wherein the carbopol formulations serve as a source of protons and as a viscosity agent.

Just before use, Parts A and B are mixed together in a 1:1 ratio by volume, then loaded directly into the lumen site of the indwelling implant device as discussed above, or presented into a tube or reservoir in which the insert rod has been placed for loading of the newly formed free iodine into the rod prior to its insertion into the lumen of the device to which anti-infective activity is to be conferred. In the latter instance, the insert rod should be allowed to remain exposed to the iodine generating solution until it takes on a violet to red hue indicative of iodine transfer to the solid phase of the insert rod. The insert rod is then removed from the solution and inserted into the inner lumen of the implant device to affect transfer of preloaded free iodine to the implant device.

Where it is desirable to exclude a viscosity agent in Part B of the formulation (for example, for use in an indwelling venous catheter), citrate or alkali salt phosphate buffers ranging from not less than 1 mM nor in excess of 50 mM, preferably of about 10 mM, ranging in pH from about 3.5 to about 6.0, preferably about pH 4.5, in sterile water, may be substituted in place of carbopol. The choice of the pH donor is not critical so long as the buffer system is not toxic given intravenously to the body, or not an irritant in coming into contact with the epithelial tissues of the body.

Appropriate intervals of preloading the insert rod, and for allowing free iodine to transfer to the implant device must be worked out on a case by case basis depending upon the nature of the device to be loaded, but in general the process should be completed within a period of not less than about 1 minute, nor more than about 30 minutes to be practical in the clinical setting. If the loading formulation is to be left within the implant, or the insert rod is designed to be left in the implant lumen (i.e., fabricated to allow fluids to flow freely around the insert and inner walls of the lumen) then it is only necessary to assess timing with regard to the frequency of treatments in preventing and/or treating implant infections linked with the insertion of the implant and its retention in the body cavity for which it is in use.

Hydrogels other than Carbopol may be substituted in its place in Part B of the iodine generating formulation such as carboxy methylcellulose, hydromethylcellulose, hydroxypropyl cellulose, polyethylene glycols, and the like. The main purpose of the hydrogel is to provide a more viscous fluid in preventing rapid expulsion of the iodine generating formulation from the site of its deposition within the lumen of the medical device to be treated with anti-infective activity. Similarly, the choice of oxidant is not critical providing the oxidant is stable in the aqueous formulation in providing Part B with sufficient shelf life to make its use practical for commercial use. Inorganic oxidants or preferred in this regard, such as iodate salts, since these salts are stable in solution as formulated for several months without adverse loss of oxidizing activity in converting inorganic iodide to iodine under the conditions noted above.

The present invention thus offers substantial flexibility in providing for stable two-component formulations which, when delivered to the inner lumenal wall of catheters, and other implant devices, fabricated from hydrophobic polymers such as silicone, polyurethane, polyvinyl chloride, or polyethylene, and similar types of medical grade polymers used commonly in medical implants devices, confer to such devices anti-infective activity. This anti-infective activity is conferred by the rapid transfer of free elemental iodine into, and across, the walls of such implant devices, presenting to the exterior surfaces of such devices a concentration of iodine in excess of 2 ppm sufficient to kill microorganisms adhering and adjacent to the outer walls of the devices subjected to such treatment. Furthermore, the invention provides flexibility in dosing implant devices with anti-infective activity by allowing for in situ de novo formation of free elemental iodine within and about the walls of implant devices treated by the invention. Contrary to prior art, the invention teaches that binding agents, or iodophors, are unnecessary in coating the walls of implant devices to be treated, and indeed that the latter treatments are contraindicated. Free iodine dosing and egress from the implant device, as illustrated in the accompanying examples, is easily controlled by selection of the available concentration of precursor inorganic iodide formulated in the invention which, in combination with an oxidizing agent, and proton source, ensures rapid conference of anti-infective activity to implant devices using this invention. This invention is applicable in treating existing catheter devices such as urinary catheters, venous and arterial access lines, drain tubes, as well as solid implant devices where rapid self-sterilizing activity conferred to the implant device is desirable in reducing the incidence of infections otherwise introduced during, and after, implantation in body cavities.

SPECIFIC EXAMPLES

Example 1

Effect of pH on De Novo Formation of Elemental Iodine Produced from Inorganic Iodide and Iodate. FIG. 1 shows the effect of varying the pH of buffered citrate solutions (50 mM) on the rate of free elemental iodine formation using potassium iodide and sodium iodate as precursors. Iodine was quantitated as the triiodide complex formed by transfer of aliquots of test reaction mixtures to stock 10 mM potassium iodide made up in distilled water measured at 350 nm on a double-beam UV-265 double beam Shimadzu spectrometer. A calibration curve was prepared using crystalline iodine dissolved in the same stock potassium iodide solution. Citrate buffered solutions were made up to known pH values as indicated, determined by titration and measurement on a standard pH meter. Aliquots of the citrate buffered solutions were mixed with silicone discs impregnated with a mixture of 2% potassium iodide and 10% sodium iodate (by weight relative to the disc). Following varying incubation periods, aliquots of the test solutions were analyzed for formation of elemental iodine as noted above from which a pH profile was constructed showing the rate of free iodine formation versus proton concentration. The optimal pH for iodine formation was observed to be approximately 4.5 regardless of the incubation interval. Samples were monitored for iodine formation from approximately 10 minutes up to 24 hours after initiation of the reaction. FIG. 1 is typical of the pH profiles observed reflecting accumulated free iodine approximately 4 hours after initiation of iodine formation.

Example 2

Figure 2:
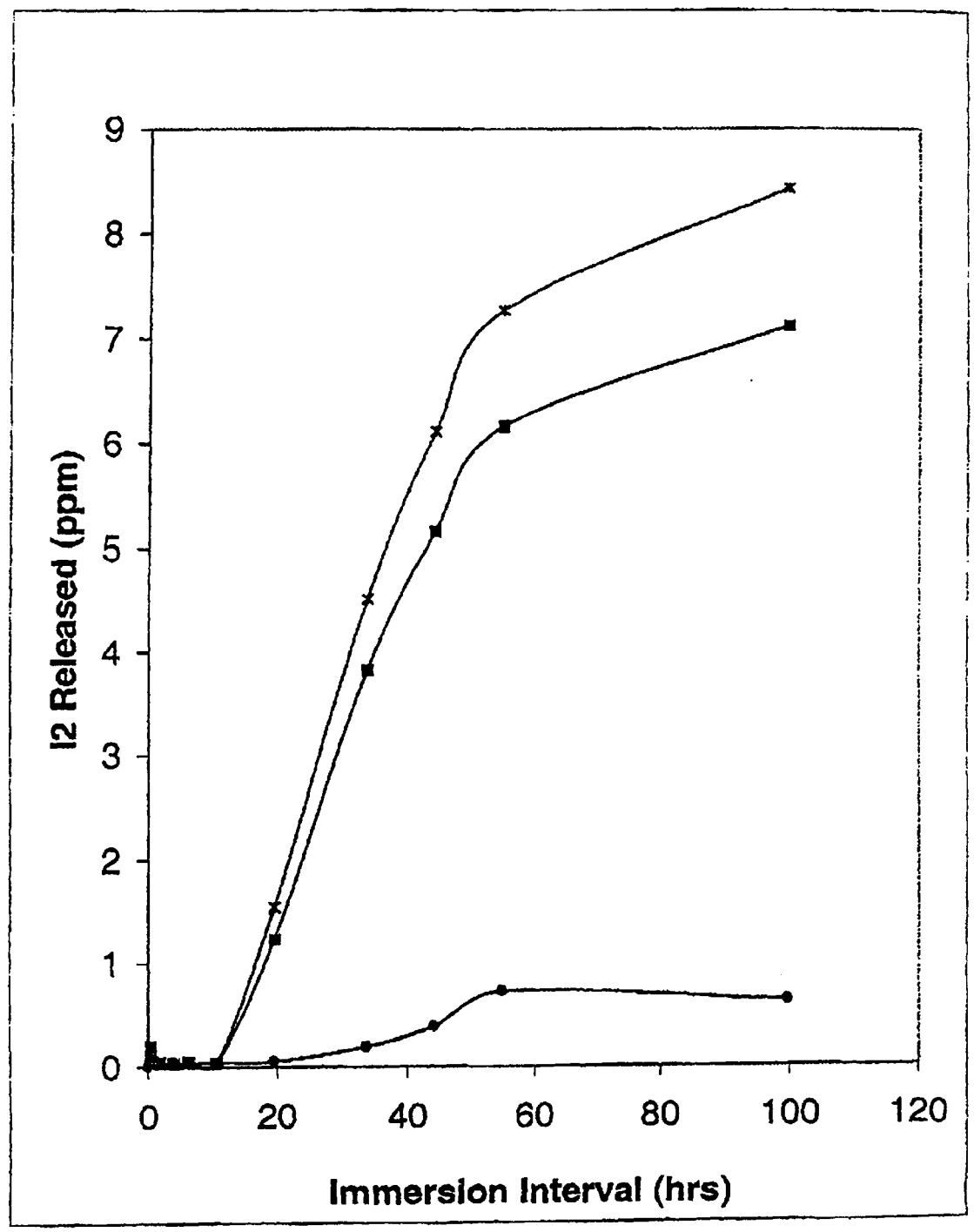
FIG. 2 shows the recovery of iodine released from polyvinylchloride (PVC) tubing preloaded with varying concentrations of iodine formed using the method of providing anti-infective activity of the invention, i.e., in-situ chemical anti-infective loading technology (herein after "ICAT") for iodine generating formulations versus immersion times of the catheter in oxidant generating formulations (i.e., "ICAT fluid"). Five cm lengths of PVC tubing (outer diameter, 5.5 mm; inner diameter, 3.0 mm) were preloaded with iodine generating formulations made up of parts A and B in which the final concentration of inorganic sodium iodide ranged from 2.5 (solid circles), to 12.5 mM (solid squares) to 50 mM ("x" symbols), respectively. The final concentration of Carbopol C971 PNF was made up as 0.25%, and sodium iodate was held constant at 12.5 mM. The pH of the iodine generating formulation was 4.6.

Egress of Iodine from Polyvinylchloride (PVC)-Loaded Catheter Tubing by ICAT. FIG. 2 shows the recovery of iodine released from PVC tubing preloaded with varying concentrations of iodine using in-situ chemical anti-infective loading technology (ICAT) for iodine generating formulations versus immersion times of the catheter in fluid. Five cm lengths of PVC tubing (outer diameter, 5.5 mm; inner diameter, 3.0 mm) were preloaded with iodine generating formulations made up of parts A and B in which the final concentration of inorganic sodium iodide ranged from 2.5 (solid circles), to 12.5 mM (solid squares) to 50 mM ("x" symbols), respectively. The final concentration of Carbopol C971 PNF was made up as 0.25%, and sodium iodate was held constant at 12.5 mM. The pH of the iodine generating formulation was 4.6. Immediately after preloading the inner lumen of the PVC tubing, the ends were capped with glass rods (total ICAT loading volume, 0.353 ml), and the catheter tubing was rinsed with distilled water to remove any traces of iodine generating formulation from the exterior surfaces. Each was then immersed in 10 ml of 10 mM KI made up in water, and the egress of free iodine into the latter fluid (trapped as the triiodide complex) tracked at 350 nm on a UV-265 Shimadzu double beam spectrometer at the points indicated in FIG. 2. Quantitation of the free iodine concentrations was made by constructing a calibration curve and converting milliabsorbances measured in the external fluid to ppm using known amounts of crystalline iodine dissolved in the same potassium iodide solutions. The effectiveness of the end caps used in sealing the catheters was confirmed by loading the same tubing with dye (toluidine blue) and verifying that it did not leak into the external fluid bathing the catheter. All experiments were conducted at room temperature (~21–23° C.).

The results show an initial lag phase in the release of free iodine from the loaded catheter segments corresponding to approximately 10 to 12 hours, and a subsequent phase in which free iodine levels began to rise almost linearly with time with a subsequent tapering off of the egress rate about 3 days after the initial loading of ICAT. The rate of iodine release continued to rise gradually over an extended period of time except at the lowest loading dose used (e.g., 2.5 mM sodium iodide). In the latter case, free iodine peaked at about 55 to 60 hours after initial loading with ICAT. Peak levels of free iodine in the 10 ml external fluid volume reached the microbial killing target of about 2 ppm within the first 24 hours for sodium iodide loading doses of ICAT equal to or exceeding 25 mM. Depending upon the external fluid volume in which iodine egressing from the catheter tubing comes into contact with, it can be appreciated that more than adequate levels of microbicidal iodine were achieved to confer to the external wall and local environment potent anti-infective activity.

Example 3

Figure 3:
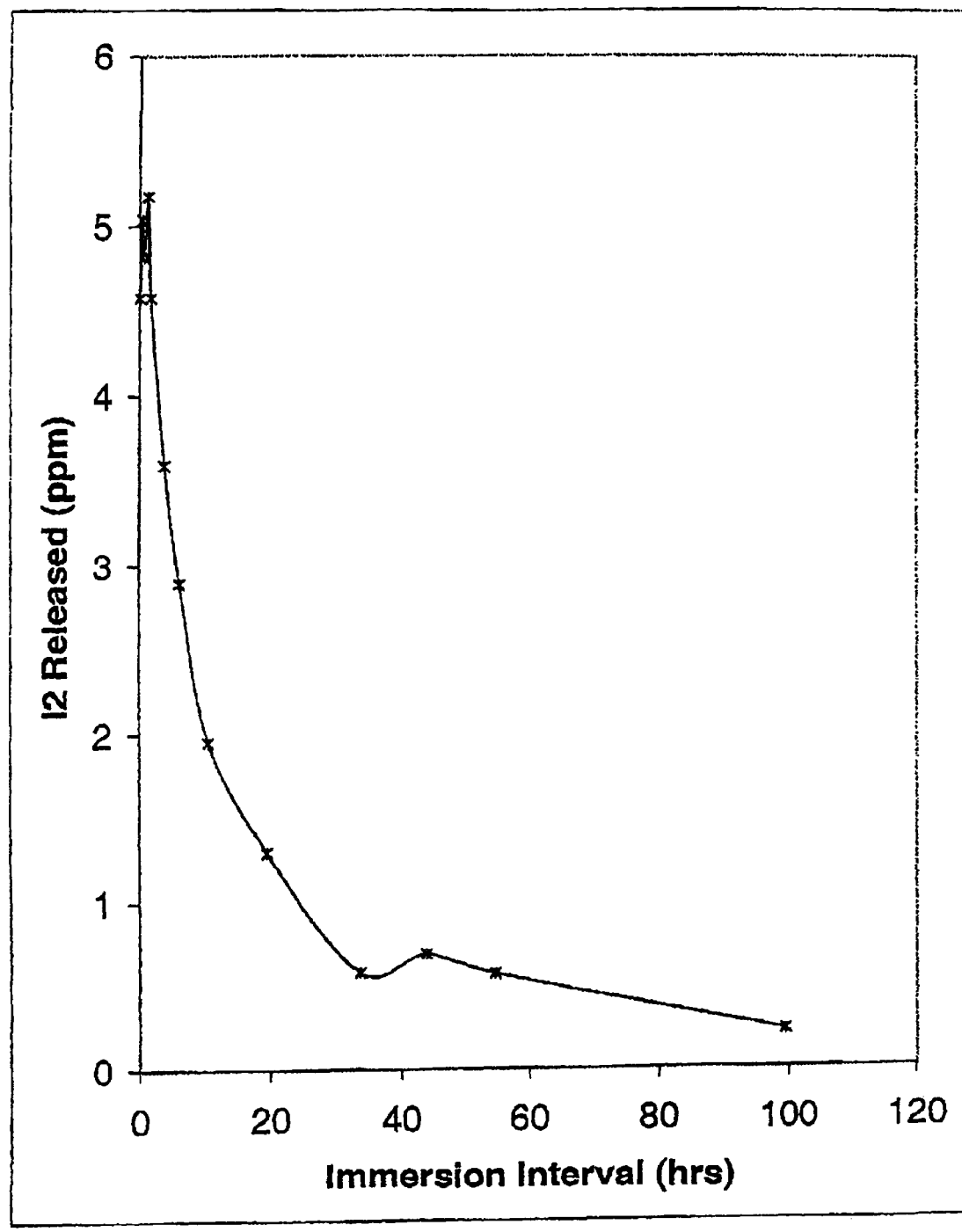
FIG. 3 shows the corresponding uptake of free iodine from the internal lumen after loading of ICAT into the same PVC tubing as in FIG. 2 using a final concentration of sodium iodide of 25 mM with sodium iodate held constant at 12.5 mM, Carbopol C971 PNF held at 0.25%, and the final pH set at 4.6. The concentrations shown in FIG. 3 represent $\frac{1}{100}^{th}$ of the actual concentration of free iodine present in the internal lumen of the catheter at the intervals indicated in FIG. 3.

Uptake and Transport of Free Iodine into the Catheter Wall of ICAT-Loaded PVC Tubing. FIG. 3 shows the corresponding uptake of free iodine formed with loading of ICAT into the same PVC tubing using an identical experimental setup as in Example 2. In these experiments, ICAT loading was made using a final concentration of sodium iodide of 25 mM with sodium iodate held constant at 12.5 mM, Carbopol C971 PNF held at 0.25%, and the final pH set at 4.6. Following end capping of the PVC catheter tubing, and rinsing of the capped tubing in distilled water, the tubing was again placed in 10 ml of 10 mM KI. However, rather than monitoring the egress of iodine, at the points indicated in FIG. 3, 10 µl aliquots of the ICAT fluid were withdrawn from the internal lumen and the level of free iodine in the latter solution determined following 100-fold dilution in 10 mM potassium iodide solution. The concentrations shown in FIG. 3 thus represent $\frac{1}{100}^{th}$ of the actual concentration of fee iodine formed in the internal lumen of the catheter.

The results of FIG. 3 show that the free iodine concentration quickly achieved saturating levels of free iodine with regard to the solubility of iodine (upper limit of solubility, ~320 ppm) in less than a few minutes of ICAT loading, and thereafter the iodine concentration fell sharply over the next several hours, reaching a slower rate of decline around 40 to 50 hours after initial ICAT loading of the catheter. The attainment of a trough around 40 hours post ICAT loading 20 within the internal lumen site, and peak egress of iodine in the range of 55 to 60 hours post ICAT loading (cf., FIG. 3), suggests that in PVC tubing the transit time of iodine passing across the walls of the catheter may be as long as 15 to 20 hours. This is also consistent with the initial lag phase in the egress of free iodine from the walls of the PVC catheters shown in FIG. 3. Except for the lag phases, FIGS. 2 and 3 show inverse relationships between the clearance of free iodine from the inner lumenal reservoir, and egress from the out walls of the PVC catheters as would be expected in a reciprocal transport process from the inner to exterior walls of the catheters. Furthermore, the high internal levels of iodine seen shortly after ICAT loading, and subsequent steep fall in iodine levels, is consistent with crystallization of iodine onto the inner walls of the catheter, and subsequent uptake of iodine into the PVC wall of the catheter.

Example 4

Figure 4:
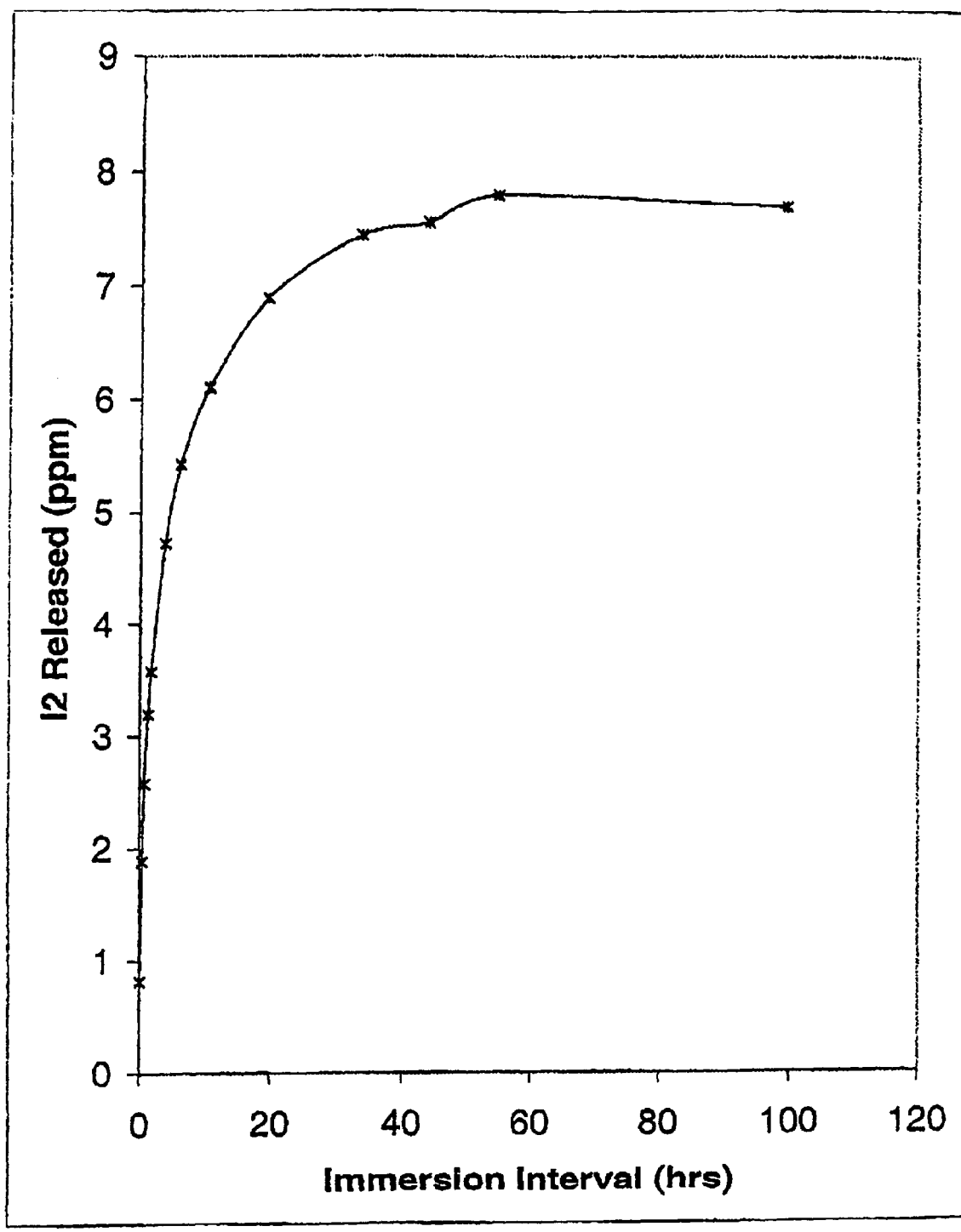
FIG. 4 demonstrates the kinetic transfer of free elemental iodine from a prefabricated hydrophobic polyethylene(PE) tab (dimensions, 8.5×0.5×0.05 cm [length×width×thickness]), loaded with free elemental iodine using ICAT technology, to free solution (10 ml of 10 mM KI). Each point on the graph reflects the level of free iodine recovered in the immersion fluid in which the PE tab was placed.

Transfer of Free Iodine from a Solid-Phase Loading Platform to an Aqueous Solution. FIG. 4 demonstrates the kinetic transfer of free elemental iodine from a prefabricated hydrophobic polyethylene (PE) tab (dimensions, 8.5×0.5× 0.05 cm [length×width×thickness]), loaded with free elemental iodine using the ICAT technology, to free solution (10 ml of 10 mM KI). In these experiments the PE tab was first exposed to ICAT (final concentration of sodium iodide, 25 mM; sodium iodate, 12.5 mM; Carbopol C971 PNF, 0.25%) at room temperature for 30 minutes. During this interval the PE tab took on a deep violet color concomitant with the formation of minute crystalline particles of iodine condensing onto its surface, and subsequent diffusion of iodine from the solid state into the PE tab. The PE tab was then removed from the ICAT iodine loading solution, rinsed in distilled water to remove any residual iodine solution adhering to the PE tab's surface, and then placed in 10 ml of 10 mM potassium iodide made up in water to track the release of free iodine. Each point on the graph shown in FIG. 4 reflects the level of free iodine recovered in the immersion fluid in which the PE tab was placed (measured as described in Example 1 at 350 nm). Microbial killing levels of free iodine in excess of 2 ppm were achieved with the solid-phase transfer platform within approximately 20 minutes of immersion of the PE tab in solution. Thereafter, free iodine accumulated in the immersion fluid over a period of approximately 60 hours after which the levels of free iodine reached a plateau at about 8 ppm in a total fluid volume of 10 ml.

These results confirm the feasibility of solid-phase transfer of free iodine from a solid-phase insert (e.g., the PE tab) to an aqueous fluid. It is anticipated that had the PE tab been constructed to insert within the lumenal space of an indwelling device, that the series of transfers of iodine would progress from the solid-phase insert to the internal lumenal fluid (or air phase in a free flowing urinary catheter), to the walls of the implant device, and then egress to the exterior wall of the device as illustrated in reviewing the results documented in Examples 2, 3 and 5 though 8.

Example 5

Figure 5:
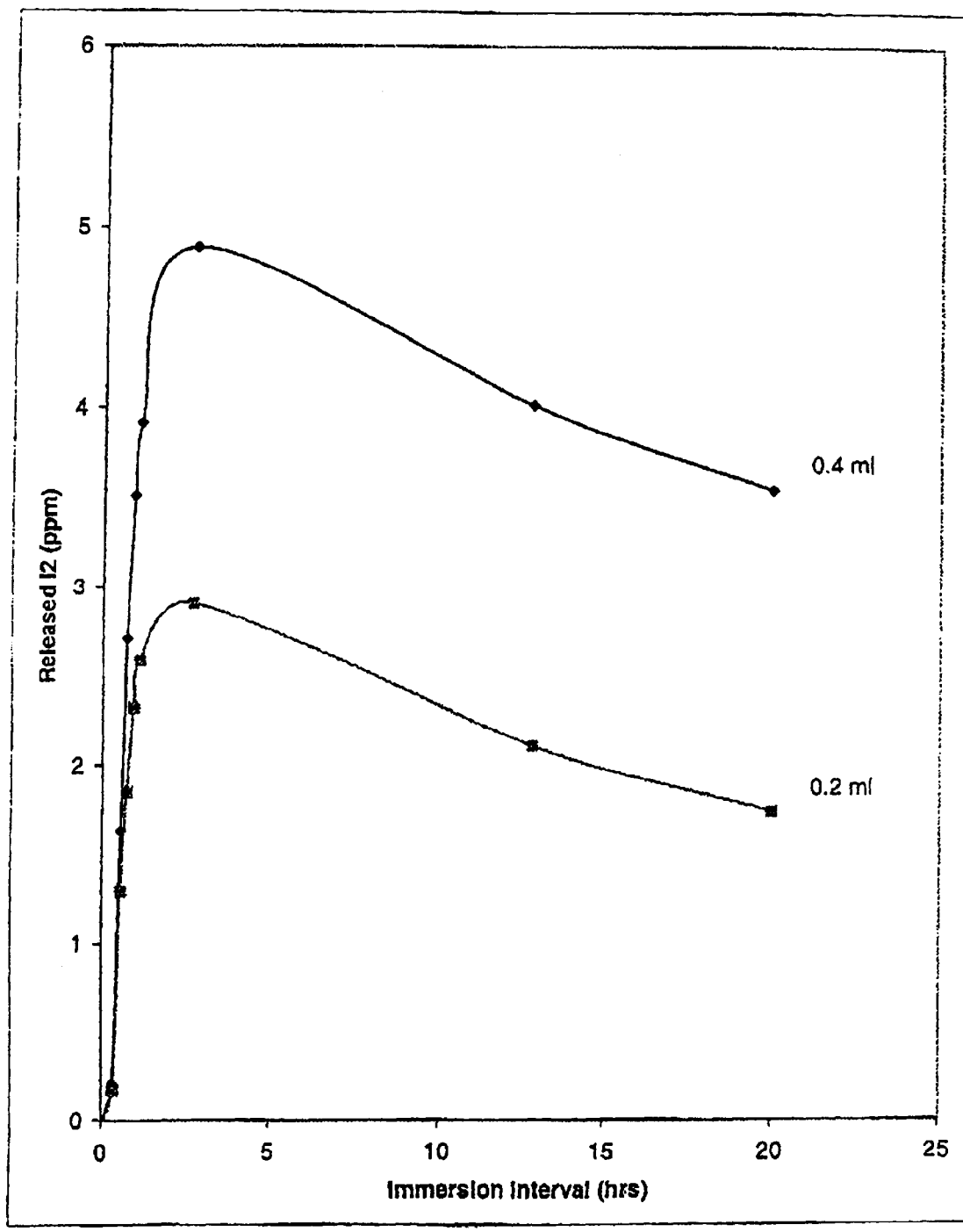
FIG. 5 shows the release rates of free iodine egressing from the exterior wall of silicone catheters preloaded for 20 minutes with ICAT iodine generating formulation. The upper tracing shows the results of iodine egress from the external walls of a catheter with a diameter twice that of the lower tracing (total ICAT fluid volumes preloaded into the catheters are indicated to the right of each tracing).

Effect Pre-Loading Volume of ICAT Iodine Generating Formulation on Iodine Egress from Silicone Catheters. FIG. 5 shows the release rates of free iodine egressing from the exterior wall of silicone catheters preloaded for 20 minutes with ICAT iodine generating formulation. Five cm lengths of all silicone catheters were prepared and loaded with a final concentration of 25 mM sodium iodide ICAT solution made up also in 12.5 sodium iodate, 1 0.25% Carbopol C971 PNF, pH 4.6, capped with glass rods on the ends, and rinsed of any residual contaminating ICAT solution on the exterior surface of the catheters. Following a 20 minute incubation period at room temperature, the residual ICAT fluid inside the catheters were flushed out with distilled water, the ends of the catheters were resealed with glass rods, and the catheters then immersed in 10 ml of 10 mM potassium iodide made up in distilled water. Thereafter, the concentration of free iodine was tracked as a function of the immersion interval in the same manner as in FIG. 2. The upper tracing shows the results of iodine egress from the external walls of the catheter using a catheter with a diameter twice that of the lower tracing (total ICAT fluid volumes preloaded into the catheters are indicated to the right of each tracing).

The results show rapid egress of free iodine from the preloaded silicone catheters with microbial killing levels of 2 ppm were achieved for both catheters within about 40 minutes of immersion after an initial 20 minute exposure of the catheter to ICAT iodine generating formulation. Peak levels of free iodine (in a fluid volume of 10 ml) occurred about the third hour of immersion with a gradual falloff in the recovery of free iodine over the next approximate 24 hours.

Example 6

Egress of Free Iodine from Silicone Catheters as a Function of ICAT Iodine Loading Dose and Immersion Interval.

Figure 6:
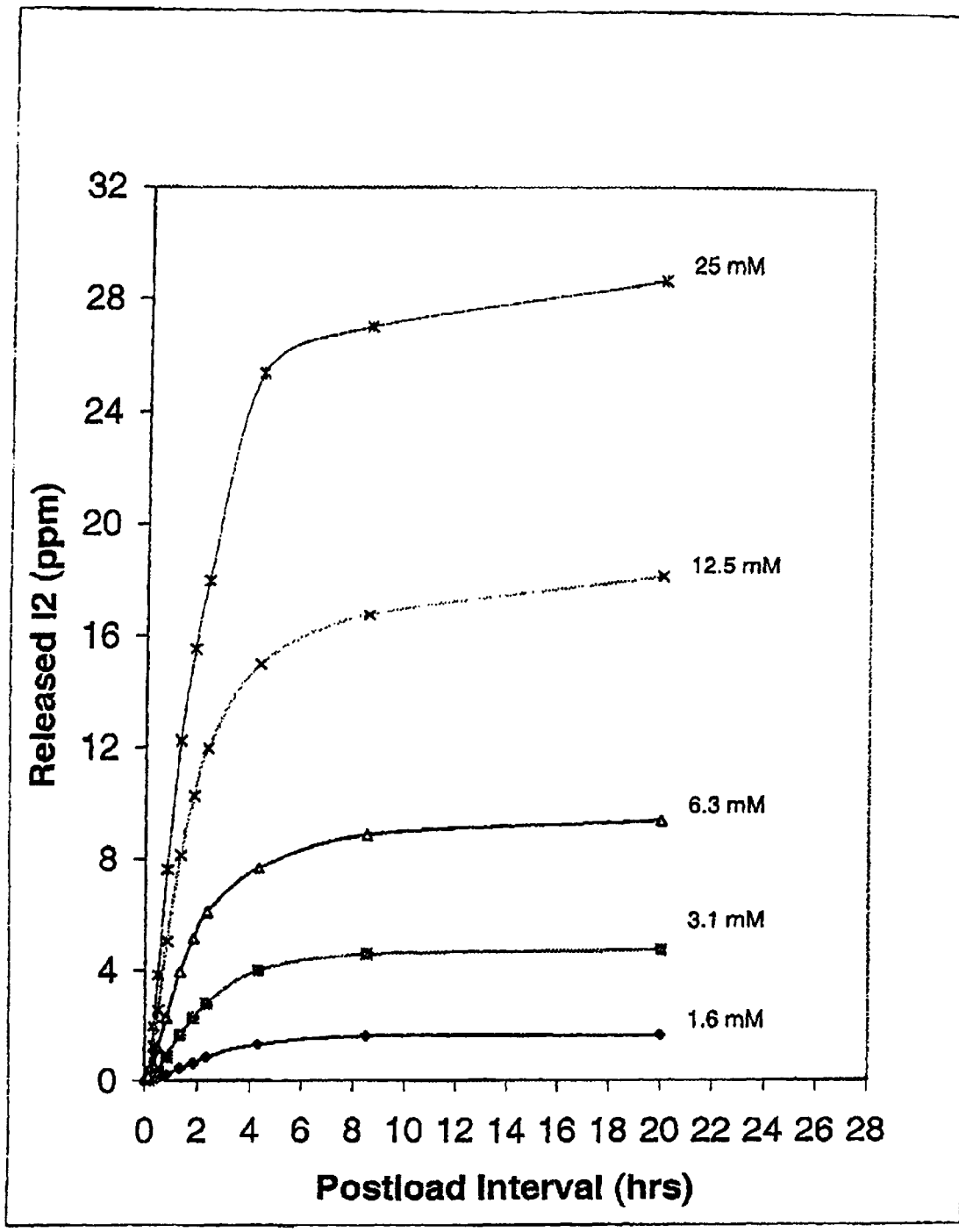
FIG. 6 shows the release of free iodine from the exterior walls of silicone catheters submerged in 10 ml potassium iodide using varying concentrations of sodium iodide in the ICAT formulation delivered to the inner lumen from a low concentration of 1.6 mM to a high of 25 mM, as indicated, as a function of immersion interval. The concentration of sodium iodate and Carbopol C971 PNF was kept constant at 12.5 mM and 0.25%, respectively.

FIG. 6 shows the release of free iodine from the exterior walls of silicone catheters cut into 5 cm lengths and capped as in Example 2, but using varying concentrations of sodium iodide from a low concentration of 1.6 mM to a high of 25 mM, as indicated The concentration of sodium iodate and Carbopol C971 PNF was kept constant at 12.5 mM and 0.25%, respectively. As in Example 2, after loading ICAT iodine generating formulations into the internal lumen of the catheters, each was sealed with glass rods and immersed in 10 ml of 10 mM potassium iodide to allow for tracking of free iodine egressing from the exterior walls as a function of immersion interval.

The rates of iodine egress were much faster in silicone catheters relative to PVC catheters (cf., FIG. 2), reaching peak levels within approximately 4 hours after immersion of the catheters in the tracking fluid. There was also a continual rise in the release of free iodine extending beyond 24 hours of immersion for catheters loaded with ICAT containing sodium iodide in excess of ~6.5 mM (cf., FIG. 6). In addition, in all but the lowest concentration of sodium iodide used, microbial killing threshold levels of about 2 ppm free iodine in 10 ml fluid volumes were achieved within roughly about one hour of immersion. The results show a linear proportionality between loading doses of sodium iodide included in the ICAT formulation and free iodine egressing from the catheters over the entire concentration range examined.

Example 7

Figure 7:
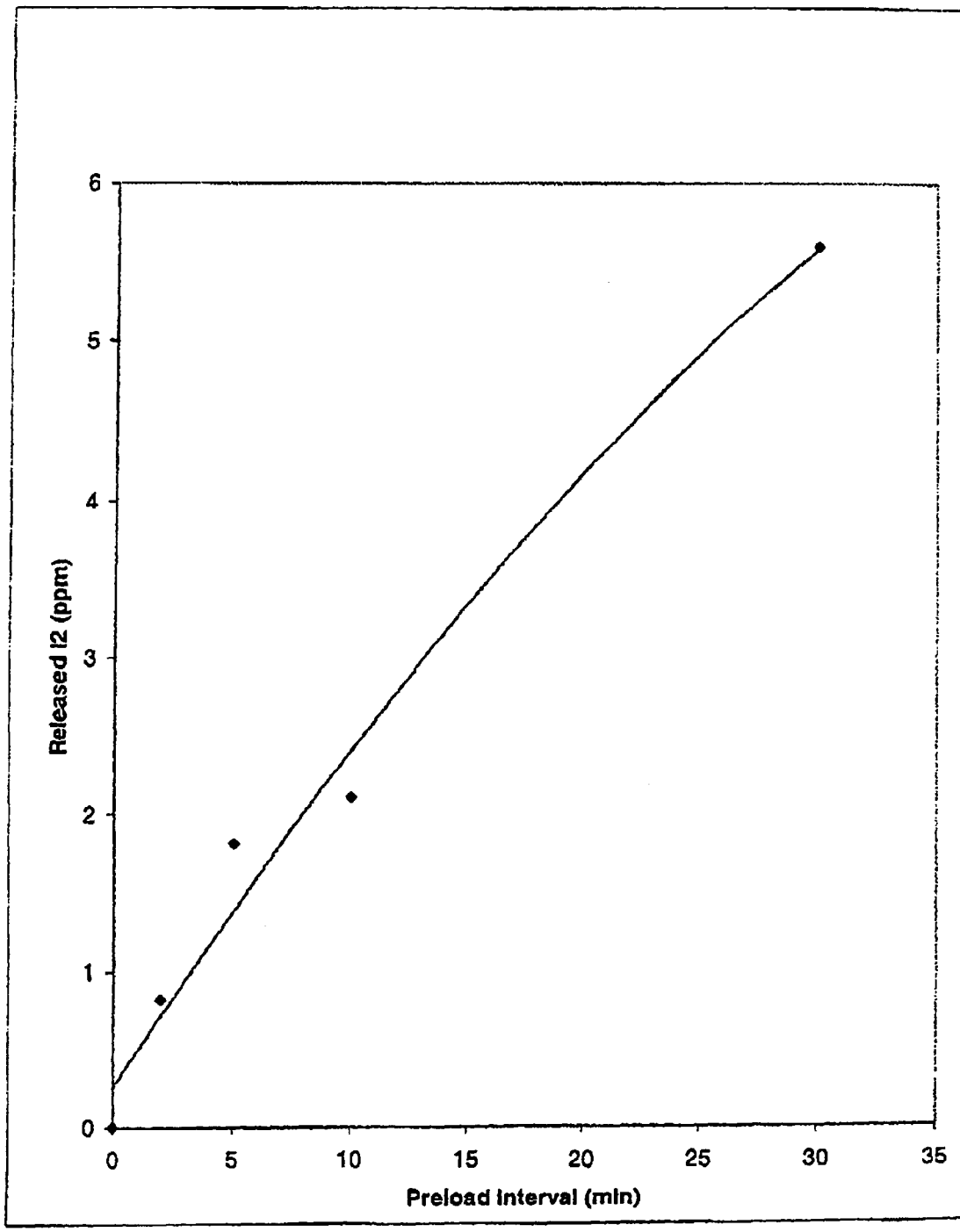
FIG. 7 shows the effect of preloading interval (residence time of ICAT within the lumen) on egress of free iodine from silicone catheters. In these experiments, 5 cm segments of silicone catheters (lumen volume, 0.2 ml) were loaded with ICAT iodine generating formulation with the final sodium iodide concentration set at 25 mM, sodium iodate at 12.5 mM, and Carbopol C971 PNF at 0.25%, for the intervals noted. Thereafter, the ICAT solutions were flushed free of the catheter with distilled water, the catheters were recapped with glass rods, then immersed in 10 ml of 10 mM potassium iodide and tracked for release of free iodine egressing from the walls of the catheter into the external fluid at 4 hours after immersion.

Effect of Preloading Interval on Recovery of Free Iodine Egressing from Silicone Catheters. FIG. 7 shows the effect of preloading interval (residence time of ICAT within the lumen) on egress of free iodine from silicone catheters prepared as in FIG. 2. In these experiments, 5 cm segments of silicone catheters (lumen volume, 0.2 ml) were loaded with ICAT iodine generating formulation with the final sodium iodide concentration set at 25 mM, sodium iodate at 12.5 mM, and Carbopol C971 PNF at 0.25%, for the intervals noted. Thereafter, the ICAT solutions were flushed free of the catheter with distilled water, the catheters were recapped with glass rods, then they were immersed in 10 ml of 10 mM potassium iodide and tracked for release of free iodine egressing from the walls of the catheter into the external fluid at 4 hours after immersion.

A near linear relationship between preloading interval and the recovery of free iodine within the external fluid bathing against the capped catheters is shown. Microbial killing levels of free iodine in excess of 2 ppm were achieved within approximately 5 minutes exposure of the catheters to ICAT. These results indicate that even brief exposure to ICAT iodine generating formulations is sufficient to confer to indwelling walls of silicone type implant devices iodine-mediated anti-infective activity (see Background of the Invention).

Example 8

Figure 8:
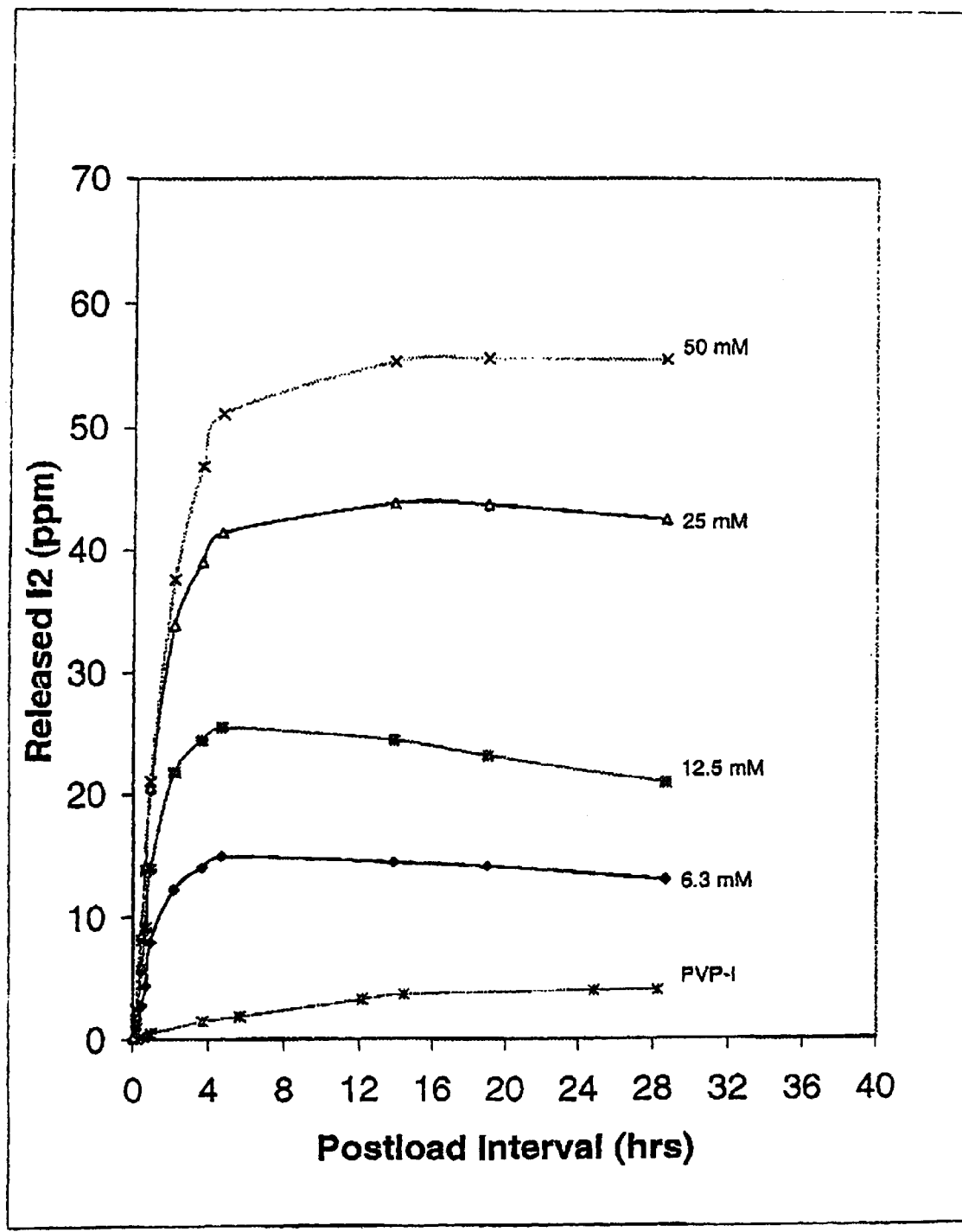
FIG. 8 shows the egress of free iodine from the walls of silicone catheters submerged in 10 ml 10 mM potassium iodide following ICAT treatment with iodine generating formulations, but with replacement of Carbopol in Part B of the formulations with 25 mM potassium citrate buffer adjusted to a final pH of 4.2. Potassium iodide in the iodine generating formulation was varied from 6.3 to 50 mM. The concentration of sodium iodate was kept constant at 12.5 mM. Also shown in FIG. 8 is the corresponding egress rate of free iodine versus submersion interval for a silicone catheter loaded with 10% Povidione-Iodine(PVP-I) substituted in place of the ICAT iodine generating formulation.

Egress of Iodine from Silicone Catheters versus ICAT Iodine Loading Dose and Immersion Interval in the Absence of a Hydrogel Viscosity Augmentor and Comparison with Commercial Povidone-Iodine Used in Place of ICAT. The egress of free iodine was examined as in Example 6 using ICAT formulations, but with replacement of carbopol in Part B of the formulation with 25 mM potassium citrate buffer adjusted to a final pH of 4.2. FIG. 8 shows the egress of free iodine as a function of potassium iodide concentration in ICAT solutions varying from 6.3 to 50 mM. The initial concentration of sodium iodate in each test was held constant at 12.5 mM. Qualitatively the release of iodine from the capped silicone tubing is very similar to that seen with carbopol wherein the release kinetics peaked at approximately 4 hours after loading the inner lumen with ICAT solutions. The data demonstrate that the level of free iodine egressing from the walls of the catheter can be adjusted over a wide range of doses from a low of a few ppm to in excess of 50 ppm (in a 10 ml suspension). Hence, total free iodine released within the first 4 hours exceeded 500 micrograms per 5 cm segment of silicone tubing loaded with ICAT solution. This contrasts sharply with the marginal release of no more than a few micrograms of free iodine over the same interval using silicone catheters loaded with 10% Povidione-iodine (cf., FIG. 8, bottom tracing). It can be seen from an examination of the experimental data (cf., FIG. 8) that within the first hour of treatment that the level of free elemental iodine egressing from the catheter tubing using ICAT exceeded that detected using 10% Povidone-iodine by a factor in excess of 50-fold. During this interval, the concentration of free iodine recovered in the suspending medium barely reached 0.4 ppm using Povidone-iodine as the means of transferring iodine to the walls of the silicone catheter, a concentration well below the necessary threshold of about 2 ppm required for effective antimicrobial activity (cf., LeVeen et al. (1993) Gynecology & Obstetrics 176: 183–190). This contrasts sharply with levels of free iodine measured in the external medium using ICAT as the loading vehicle which, under the same experimental conditions, yielded concentrations ranging from a low of 8 ppm to a high of 20 ppm, depending upon the initial formulation of inorganic iodide used (cf., FIG. 8).

Example 9

Figure 9:
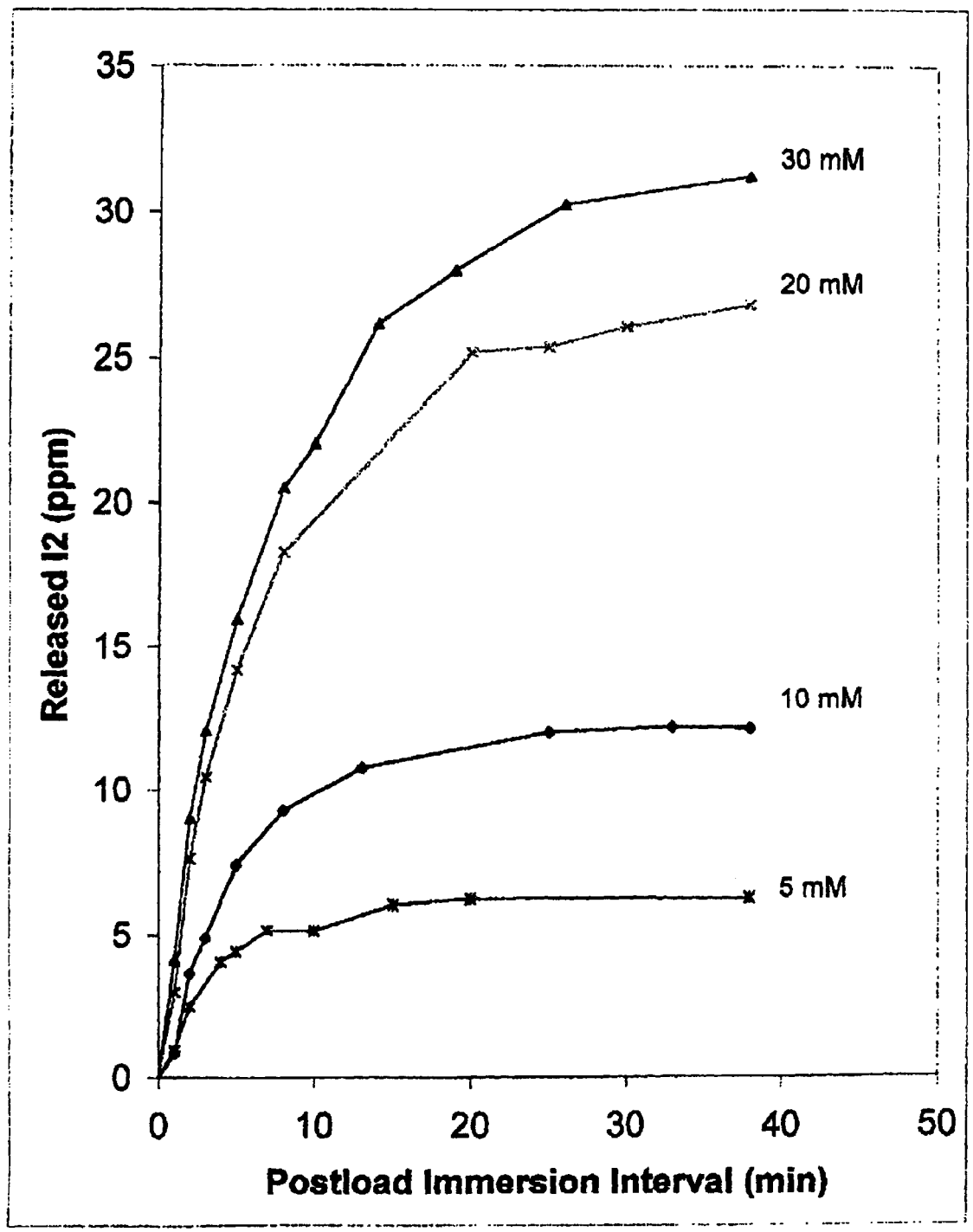
FIG. 9 shows the release of free iodine from the external walls of a McComb neonatal catheter as affected by varying potassium iodide concentrations formulated in ICAT iodine generating solutions to which the catheter was initially exposed. To test the efficacy of transiently loading iodine into the polymer base of the McComb catheter (Model NNCR3, Phoenix Biomedical Corp, Valley Forge, Pa.) using ICAT, solutions were made up at varying concentrations (final concentration after mixing parts A & B together) of potassium iodide as indicated in FIG. 9 while holding the final concentration of sodium iodate and potassium citrate at 12.5 and 25 mM, respectively. The solutions were buffered to pH 4.2. The catheter was submerged in ICAT solutions of varying potassium iodide concentration and incubated for 20 minutes. Thereafter, the catheter was rinsed in distilled water and transferred to 10 ml solutions of 10 mM potassium iodide placed inside a capped polycarbonate tube. At varying intervals the egress of preloaded iodine taken up by the catheter was measured In these measurements the inner reservoir of the catheter was capped with a nylon plug so that only the egress of iodine from the exterior side of the catheter was tracked.

Conveyance of Anti-infective Activity to a McComb Neonatal Catheter and Effect of Varying Potassium Iodide Concentrations in Affecting Iodine Uptake into the Catheter. To test the efficacy of transiently loading iodine into the polymer base of a neonatal McComb catheter (Model NNCR3, Phoenix Biomedical Corp, Valley Forge, Pa.) using ICAT, solutions were made up at varying concentrations (final concentration after mixing parts A & B together) of potassium iodide as indicated in FIG. 9 while holding the final concentration of sodium iodate and potassium citrate at 12.5 and 25 mM, respectively. The solutions were buffered to pH 4.2. The McComb catheter is a drain tube designed for treatment of hydrocephalus. It has an outer diameter of 2.1 mm, and inner diameter of 1.0 mm, a length of 3 cm, and a small inner reservoir holding about 0.1 5 ml fluid volume, all fabricated out of a platinum catalyzed silicone base polymer, and backed by a polyester patch for suturing at its implant site within the brain. It comes with a nylon plug which can be inserted into the reservoir aperture to block fluid travel through the inner lumen. The catheter was submerged in ICAT solutions of varying potassium iodide concentration prepared fresh at room temperature and incubated for 20 minutes. Thereafter, the catheter was rapidly rinsed in distilled water and transferred to 10 ml solutions of 10 mM potassium iodide placed inside a capped polycarbonate tube. At varying intervals the egress of preloaded iodine taken up by the catheter was measured as the tri-iodide complex spectroscopically at 350 nm. FIG. 9 shows a dose dependent relationship between available potassium iodide made up in the ICAT solutions and the recovery of iodine transferred to the polymer base and subsequently released into solution following the preloading interval of 20 minutes. In these measurements the inner reservoir of the catheter was capped with the nylon plug so that only the egress of iodine from the exterior side of the catheter was tracked. The egress rate from the exterior side of the catheter of iodine preloaded onto the catheter peaked around 30 minutes.

Figure 10:
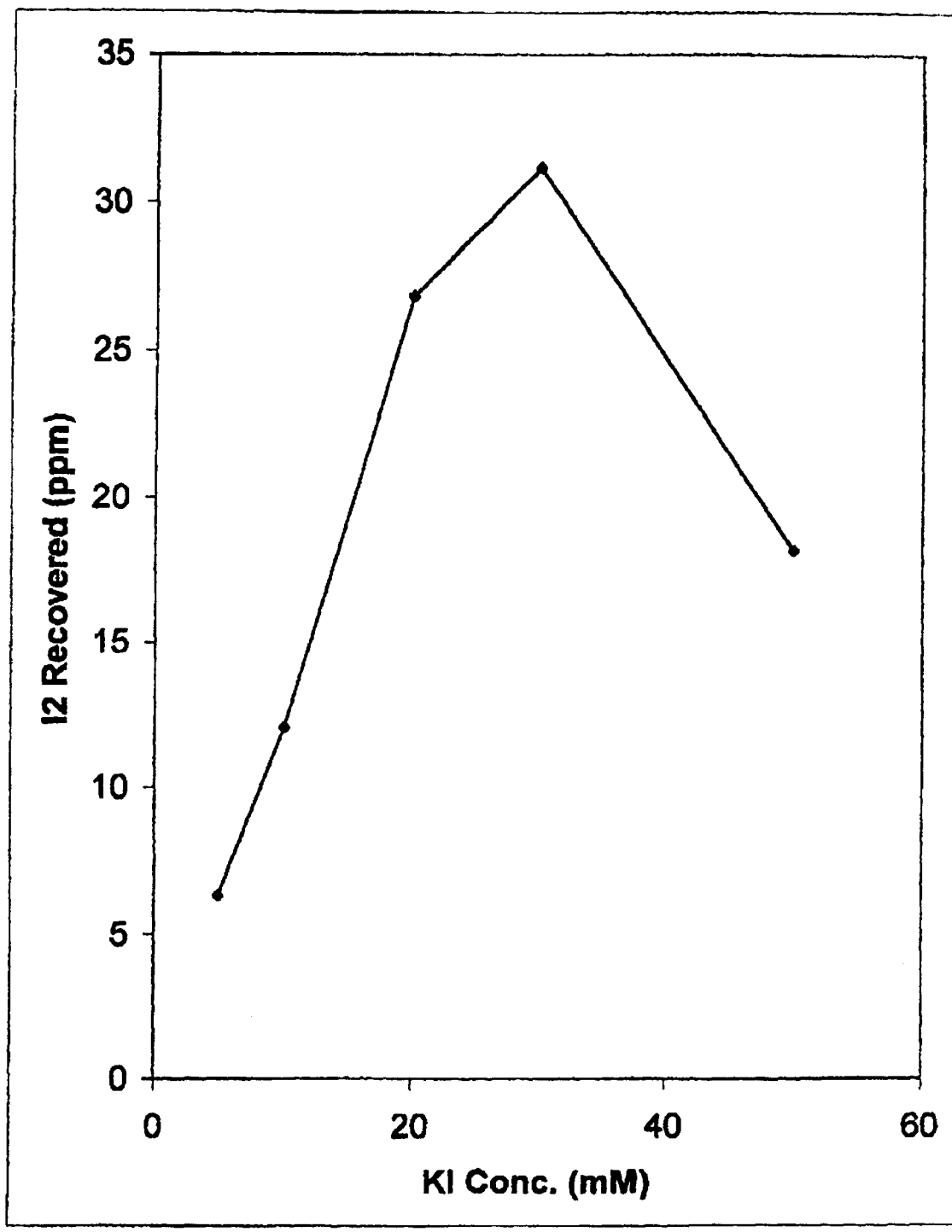
FIG. 10 shows the egress rate (and "hook" effect—see example 9) of free iodine from the external walls of McComb catheters pretreated with ICAT iodine generating formulations made up at varying concentrations of potassium iodide. The maximum recovery of iodine peaked around 30 mM potassium iodide yielding about 30 ppm free iodine (in a 10 ml fluid volume) coming back off of the polymer base approximately 40 minutes after rinsing the catheter free of ICAT iodine generating solution.

FIG. 10 shows that with increasing concentrations of potassium iodide included in the ICAT formulation, there was an actual decrease in loading efficiency of free iodine into the walls of the polymer evident by a bell shaped curve. The maximum recovery of iodine peaked around 30 mM potassium iodide yielding about 30 ppm free iodine (in a 10 ml fluid volume) coming back off of the polymer base approximately 40 minutes after rinsing the catheter free of ICAT solution The bell shaped curve affirms that loading is most efficient wherein iodine is in an unbound form. Hence, at the higher concentrations of iodide formulated into the ICAT solution where the molar ratio of iodide to iodate exceeds about 2.5, a significant portion of the iodine formed is complexed as tri-iodide which does not readily allow for the transfer of iodine into the walls of the catheter. This observation reaffirms that iodofors, or complexes of free iodine as in Lugol type solutions where tri-iodide is a dominant component, teaches away from the correct art of striving to optimize the generation of a preponderance of free iodine in maximizing its transfer to polymeric implant devices.

To verify microbial killing, the McComb catheter was preloaded with ICAT containing a final concentration of 25 mM potassium iodide, 12.5 mM sodium iodate, and 25 mM potassium citrate, pH 4.2, for 20 minutes at room temperature, then thoroughly rinsed 10 times in sterile distilled water to remove any traces of residual ICAT solution adhering to the catheter walls. *Staphalococcus epidermidis* (~$10^4$ CFU) in a total volume of 0.13 ml suspended in isotonic saline, and in BHI medium (pH 7), was then loaded into the inner reservoir of the catheter, and at one hour and four hours after loading the catheter the inner reservoir was cultured on blood agar plates for surviving organisms. In isotonic saline all of the organisms were killed within the first hour following introduction of cultures to the ICAT treated catheter. Cultures suspended in BHI media were not killed within the first hour, but by four hours no detectable organisms were recovered from the inner reservoir indicating complete killing by this time. The delayed killing seen in BHI medium appears to be attributable primarily to the high reducing equivalents in the medium which neutralizes some of the free iodine preloaded into the walls of the catheter. Nevertheless, the sustained release of iodine taken up into the walls of the catheter within the first 20 minutes ICAT treatment ultimately succeeded in killing the organisms as noted in the four hour sampling of the reservoir chamber.

Example 10

Transfer of Nascent Iodine across the Walls of Inflatable Balloons Built into Latex and Silicone Foley Catheters. Since many implant devices use inflatable balloons to hold the implant in place, the efficacy of transferring nascent iodine (formed by ICAT) across the walls of the balloon to confer to the external side of the implant anti-infective activity was examined. Foley catheters were inflated through a valve familiar to those using this type of device. In this example, ICAT solutions were substituted in place of distilled water, allowing for the transfer of nascent iodine across the walls of the catheter and balloon The addition of ICAT to the balloon involved the same process used in filling the balloon with distilled water, namely injection of fluid using a needle-free Luer-lock syringe placed into the value and expression of fluid through the cannular line communicating with the balloon. FIG. 1 1 illustrates the design of the catheter allowing for inflation of the balloon with ICAT. The small arrows perpendicular to the plane of the catheter and walls of the balloon represent lateral egress of nascent iodine from the external walls of the catheter. In this design only nascent, anti-infective, free iodine, egressing laterally across the walls of the catheter, comes into contact with body fluids and tissues, and upon egress sterilizes the latter external sites proximal to the catheter.

In this example, ICAT can be used to provide transient delivery of nascent iodine across the walls of the catheter through the inner lumen communicating with the balloon, and the walls of the balloon, itself (cf., FIG. 11). Iodine egressing in this manner into urine contained in the bladder thus serves to sterilize the bladder, providing a means of therapeutically treating cystitis. It also serves to sterilize the urethral canal through which the Foley catheter travels. This occurs as iodine moves laterally across the lumenal wall in communicating fluid to the balloon, but also as iodine delivered to the bladder urine travels down the central lumen of the Foley catheter toward the waste line.

Figure 15:
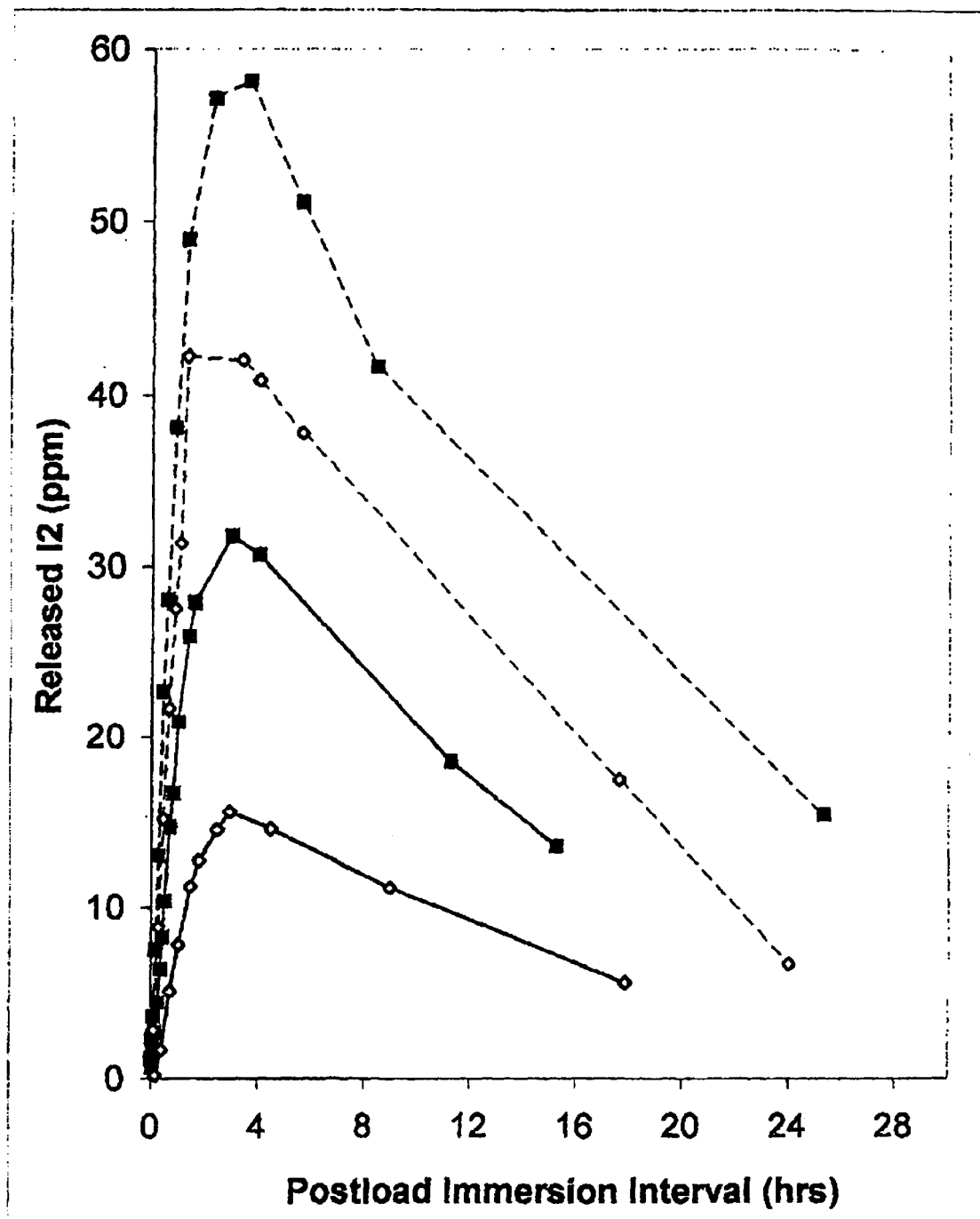
FIG. 15 shows the kinetic egress of nascent iodine from the external balloon walls of Foley catheters made of silicone (dashed line) and latex (solid line) inflated with ICAT iodine generating solutions. The ICAT solutions were formulated at a fixed concentration of iodate (12.5 mM) and potassium citrate (25 mM), and potassium iodide was adjusted to either 30 mM (solid symbols), or 15 mM (open symbols). To initiate transfer of nascent iodine formed by ICAT to the Foley catheters, 5 ml of "Part A" ICAT (either 30 or 60 mM potassium iodide made up in distilled water, as indicated) was premixed with 5 ml of "Part B" ICAT (50 mM potassium citrate, pH 4.2, made up in 25 mM sodium iodate in distilled water). This mixture was immediately transferred to a 10 ml Luer lock syringe and injected through the Luer lock type connector or valve of the Foley catheter resulting in inflation of the catheter balloon. The inflated balloon was then submerged beneath 100 ml 10 mM potassium iodide within a glass jar in which a magnetic mixing bar was also included to facilitate uniform mixing and sampling of solution coming into contact with the external side of the balloon wall. Values shown represent recovered free iodine in the solution bathing the inflated balloon at the times indicated.

FIG. 15 shows the kinetic egress of nascent iodine from the external balloon walls of Foley catheters made of silicone (dashed line) and latex (solid line) inflated with ICAT. The ICAT solutions were formulated at a fixed concentration of iodate (12.5 mM) and potassium citrate (25 mM), and potassium iodide was adjusted to either 30 mM (solid symbols), or 15 mM (open symbols). To initiate transfer of nascent iodine formed by ICAT to the Foley catheters, 5 ml of "Part A" ICAT (either 30 or 60 mM potassium iodide made up in distilled water, as indicated below) was premixed with 5 ml of "Part B" ICAT (50 mM potassium citrate, pH 4.2, made up in 25 mM sodium iodate in distilled water). This mixture was immediately transferred to a 10 ml Luer-lock syringe and injected through the valve of the Foley catheter resulting in inflation of the catheter balloon with ICAT. Nascent iodine begin forming immediately upon mixing Parts A and B ICAT solutions together, and continued to form over the next approximate four hours while the mixture resided within the inflated balloon of the Foley catheter.

For the latex catheters, standard 16 Fr. 5 cc ribbed balloon "Lubricious" Foley coated catheters were used (BARDEX® LUBRICATH® Foley Catheters, C.R. Bard, Inc., Covington, Ga. 30014). For silicone, 16 Fr. 5 cc silicone Foley catheters obtained from the same manufacturer were used (BARDEX® All-Silicone Foley Catheters, C.R Bard, Inc., Covington, Ga. 30014). Each catheter was inflated to 10 ml in volume in accordance with the volume recommendations of the catheter manufacturer, substituting ICAT in place of distilled water. The inflated balloon was then submerged beneath 100 ml 10 mM potassium iodide within a glass jar in which a magnetic mixing bar was also included to facilitate uniform mixing and sampling of solution coming into contact with the external side of the balloon wall. The remaining portion of the catheter was draped above the glass jar in a manner excluding any possibility of siphoning or leakage of ICAT solution loaded through the valve from gaining access to the potassium iodide-iodine trapping solution. At the times indicated, aliquots of the potassium iodide-iodine trapping solution bathing the balloon were drawn for measurement of nascent iodine egressing into the solution where it formed upon contact with the external solution a tri-iodide complex. Formation of tri-iodide was tracked spectrally at 350 nm. Free iodine in the external trapping solution was calculated by comparing the absorbency of test samples against that obtained for a standard curve calibrated with iodine of known concentrations added to stock potassium iodide solutions.

Peak levels of free iodine in ICAT inflated catheters occur approximately four hours after loading of ICAT into the balloon (cf., FIG. 15). The sharp falloff in nascent iodine thereafter reflects loss of free iodine into the atmosphere as iodine escapes from the trapping solution during the course of these measurements. Hence, accounting for the loss of nascent iodine to the atmosphere, it is apparent that substantial concentrations of free iodine in excess of 50 ppm (in a 100 ml fluid volume) for silicone catheters and 30 ppm for latex catheters, was achieved. Furthermore, the dosage is adjustable depending upon the concentration of inorganic iodide formulated in stock ICAT solution (Part A). Thus, this data demonstrates the feasibility of adjusting the dosage of nascent iodine delivered to the external side of the Foley catheters through introduction of ICAT to the inflatable balloon used to anchor the catheter at the base of the bladder. While in pure solutions only a few ppm free iodine are required to render a site sterile, this type of flexibility in dosing the catheter is necessary to compensate for naturally occurring reducing equivalents present in urine, and other body fluids, in contact with the walls of the catheter. Hence, through clinical evaluation and an appropriate dosage can be chosen through the frequency of ICAT delivery to the balloon, and through deliberate manipulation of the initial concentration of iodide formulated in ICAT solutions activated with mixing of Parts A and B of the stock formulation.

Example 11

Method for Delivery of Anti-Infective Iodine to Vascular Access Lines at Doses Sufficient to Kill Microbes Adhering and Propagating on Access Lines and Implant Ports while Maintaining Safe Dosage for Direct Presentation to Blood and Systemic Circulatory System: Since all materials used for the de novo generation of free iodine using ICAT are natural constituents of the body, the salient issue regarding safety to the user while achieving anti-infective activity is to ensure that total daily iodine exposure to the body does not exceed a range significantly above the generally regarded safe threshold (e.g., no more than 2-fold this threshold). Effective microbial killing occurs at not less than 0.1 ppm free iodine, preferably 5 to 10 ppm. However, the presence of reducing substances in blood and body fluids consumes free iodine, converting it to inorganic iodide. Hence, measures are required to compensate for reducing substances in blood and body fluids to achieve a final concentration of free iodine within the range stated above, or higher, to affect microbial killing and sterilization of the implanted access line, or implant port. However, an upper daily threshold for total iodine exposure of $\leq 1000$ micrograms per day is generally agreed to pose no significant health threat to human health. The principal target of excess and chronic iodine exposure is the thyroid gland wherein excess total body iodine exposure can lead to a multitude of thyroid disorders including, with chronic exposure, hyper- and hypo-thyroidism.

TABLE 1

Representative Vascular Access Line and Implant Port Inner Lumen Volumes.

| Catheter | Inner Diameter (cm) | Length (cm) | Vol. (ml) |
| --- | --- | --- | --- |
| Hohn 4F Single-Lumen CVC | 0.07 | 34 | 0.131 |
| Hohn 5F Single-Lumen CVC | 0.09 | 34 | 0.216 |
| Hohn 7F Dual-Lumen CVC | 0.08 | 36 | 0.181 |
| Hohn 7F Dual-Lumen CVC | 0.1 | 36 | 0.283 |
| SLIMPORT ® Implant Port | 0.13 | 75 | 0.995 |
| ROSENBLATT Dual SLIMPORT ® Implant Port | 0.1 | 75 | 0.589 |
| PER-Q-CATH ® (Dual-Lumen) PICC | 0.03 | 60 | 0.042 |
| PER-Q-CATH ® (Dual-Lumen) PICC | 0.063 | 60 | 0.187 |

Table 1 illustrates that vascular access lines (cf., central venous catheters (CVC) and peripherally inserted central venous catheters (PICC)), and implant ports (cf., SLIMPORT® and a ROSENBLATT implant ports) have small diameters by design as an essential aspect in allowing for these devices to be inserted into a body blood vessel for delivery of medications and sampling of the systemic blood system. Hence, the total inner lumenal volume of such devices is small and can be calculated as $Pi \times r^2 \times L$ where the equation represents the well-known geometrical calculation for the volume of a cylinder, r=the radius of the inner diameter of the implant lumen, and L=the length of the implant device. Using these calculations it can be seen that the total volume of the inner lumens of the representative implant devices cited in Table 1 range from 0.042 ml to approximately 1 ml.

The total iodine load presented by direct delivery of ICAT into the inner lumen of a device can be calculated as the volume flushed into the device multiplied by the concentration of total iodine (free iodine, inorganic iodide, and oxides of iodide) in the ICAT solution. Based upon the small internal lumen size of vascular access lines and implant ports (cf., Table 1), and the calculation noted, the safe daily thresh-hold of total iodine presented to the implant of $\leq 1000$ micrograms per treatment on any given day (1 ppm=1 microgram per ml) in the delivery 5 of free iodine poses no significant safety hazards to a user in terms of iodine exposure. This can be seen for ICAT formulated at 12.5 mM sodium iodate, 30 mM sodium iodide, and 12.5 mM sodium citrate, pH 4.2, for example, which generates up to 200 to 300 ppm free iodine within approximately 20 minutes of activation. Since total iodine for this formulation for a 1 ml volume of the ICAT mixture is 2697 micrograms iodine, diluting this solution ten-fold in isotonic saline (0.9% sodium chloride) before infusion, and then delivering 1 ml of the diluted solution to the device lumen, allows for presentation of about 20 to 30 ppm free iodine to the inner lumen of the implant device while presenting a total body iodine exposure of no more than approximately 270 micrograms.

To rid the lumen of the implant (e.g., catheter) of reducing substances, the implant should first be flushed with isotonic saline. In this manner, microbes present in the lumen, or attached to the outer wall of the implant, can be killed as free iodine diffuses into the implant, and across the walls of the implant to the external surface. The treatment can be used at regular intervals, as necessary, to confer to vascular access lines, and ports, anti-infective activity.

Example 12

Reduction of Total Iodine Body Dose by Insertion of a Volume Occupying Insert within a Lumen to be Conferred with ICAT Anti-Infective Activity. Alternatively, where the diameter of the lumen requiring ICAT treatment, or the length of the access lumen, is such that the total volume of fluid occupying the lumen precludes safe delivery of ICAT without exposing the user to levels of iodine in excess of 1000 micrograms per day, treatment of the lumen can be accomplished by insertion of a space occupying insert within the central lumen. As noted in Example 11, a 10 ml solution of ICAT formulated as indicated contains a total iodine dose of 26968 micrograms, more than 25-fold the upper thresh-hold of ~1000 micrograms to be taken in on a daily basis. The insert can be designed, however, to displace volume in the lumen to ensure that the total fluid volume with ICAT delivered to the lumen treatment site is not less than 0.1 ml, nor more than 0.5 ml. In this manner, upon placement of the volume occupying insert within the central line, only the peripheral space between the insert and inner walls of the lumen receive ICAT treatment, and thus the total body exposure to iodine poses no health hazard since the iodine dosage delivered to the lumen cannot exceed an upper limit of approximately 1348 micrograms (e.g., 0.5 ml of ICAT solution), a level of no significant health risk to the user. This level of iodine exposure meets the essential element requirements of the body for iodine, yet free iodine formed in the range of 200 to 300 ppm is sufficient to kill microbes on the surface of the inner wall of the lumen device, and to pass through the walls of the lumen in treating bacteria which may also seed on the outside wall of the device.

The fact that the insert may touch sections of the inner wall of the lumen does not preclude conveyance of anti-infective activity throughout the walls of the device since free iodine diffuses freely within the hydrophobic polymer base of the device, filling in where direct access is not possible because of steric positioning of the insert against the lumen wall. In one embodiment, the insert has a configuration similar to the oxidant releasing member as discussed above and illustrated in FIGS. 13–14, except it preferably comprises an iodine impenetrable material, such as stainless steel, to thereby occupy space without absorbing free iodine generated by the ICAT.

Preferably the insert should occupy the full length of the lumen to be treated, contain a rounded tip to allow it to slide freely through the central lumen line in which it is inserted. The actual cross-sectional shape is not critical so long as the difference between the inner volume occupied by the insert and the total volume of the lumen is not greater than approximately 0.5 ml, or adjusted to ensure that total iodine dosage does not exceed approximately 1000 micrograms per treatment. The physical dimensions of the insert can be calculated relative to the lumen volume by the equation:

Volume ICAT Delivered=Total Lumen Volume—Insert Volume

Preferably the diameter of the insert should not be greater than 95%, nor less than 10% of the lumen diameter to allow for ease of insertion and removal. Diameters that are less than 10% of the lumen diameter do not occupy significant space, as a general rule, to justify using as an insert probe.

In the case of a round lumen of radius, r, of given length, L, wherein the insert occupies 80% of the lumen space, ICAT volume delivered to the lumen in conferring anti-infective activity to the lumen can be calculated as:

Volume of ICAT Delivered=Pi×(0.1r)$^2$×L

The total body exposure to iodine may be calculated by summing the concentrations of iodide precursors, multiplied by the molecular fraction of iodide comprising each precursor in the ICAT formulation, multiplied by the volume of ICAT delivered to the treated lumen.

Example 13

Modulation of Free Iodine Egress from the External Walls of an ICAT-Loaded Urinary Catheter through Establishment of an Equilibrium Binding Agent within the ICAT Formulation. The egress rate of free iodine across the walls of the balloon can be retarded by placing a binding agent within the liquid ICAT formulation within at least a section of the medical device, such as within the catheter balloon. The principle of modulating the egress rate through this manner is based upon setting up two competing sites for sequestration of iodine, the first the walls of the balloon, and subsequent external solution bathing the balloon into which iodine egresses, and the second, an iodine binding agent contained within the balloon. The latter establishes an equilibrium condition between free and bound iodine within the balloon, preserving and slowing down the egress of iodine from the walls of the balloon. This occurs where the binding agent is either chemically charged and therefore restricted from freely passing across the walls of the inflated balloon, where binding agent is immisicible with the polymer base making up the balloon device, or where the binding agent is of two large of molecular weight to freely permeate across the balloon wall. It is reasonably assumed that once iodine escapes to the wall of the balloon, it will pass freely to the external solution bathing the balloon, resulting in an overall net loss of free iodine contained within the balloon. As the concentration of the binding agent contained within the ICAT formulation is increased to sequester a greater proportion of free iodine formed in solution, then the iodine egress rate will be retarded based upon the Law of Mass Action and the basic principles in diffusion in which the rate of diffusion from a specific site is proportional to the concentration of the substance at that site. Suitable iodine binding agents contained within the balloon of the catheter may include silicone or mineral oils, cadexomers (carbohydrate complexes of iodine), polyvinylpyrrolidones (PVP), or other hydrophobic materials dispersed in the iodine generating formulation in a manner to represent a reservoir in binding, and thereby retarding, the egress of iodine across the catheter wall.

Figure 16:
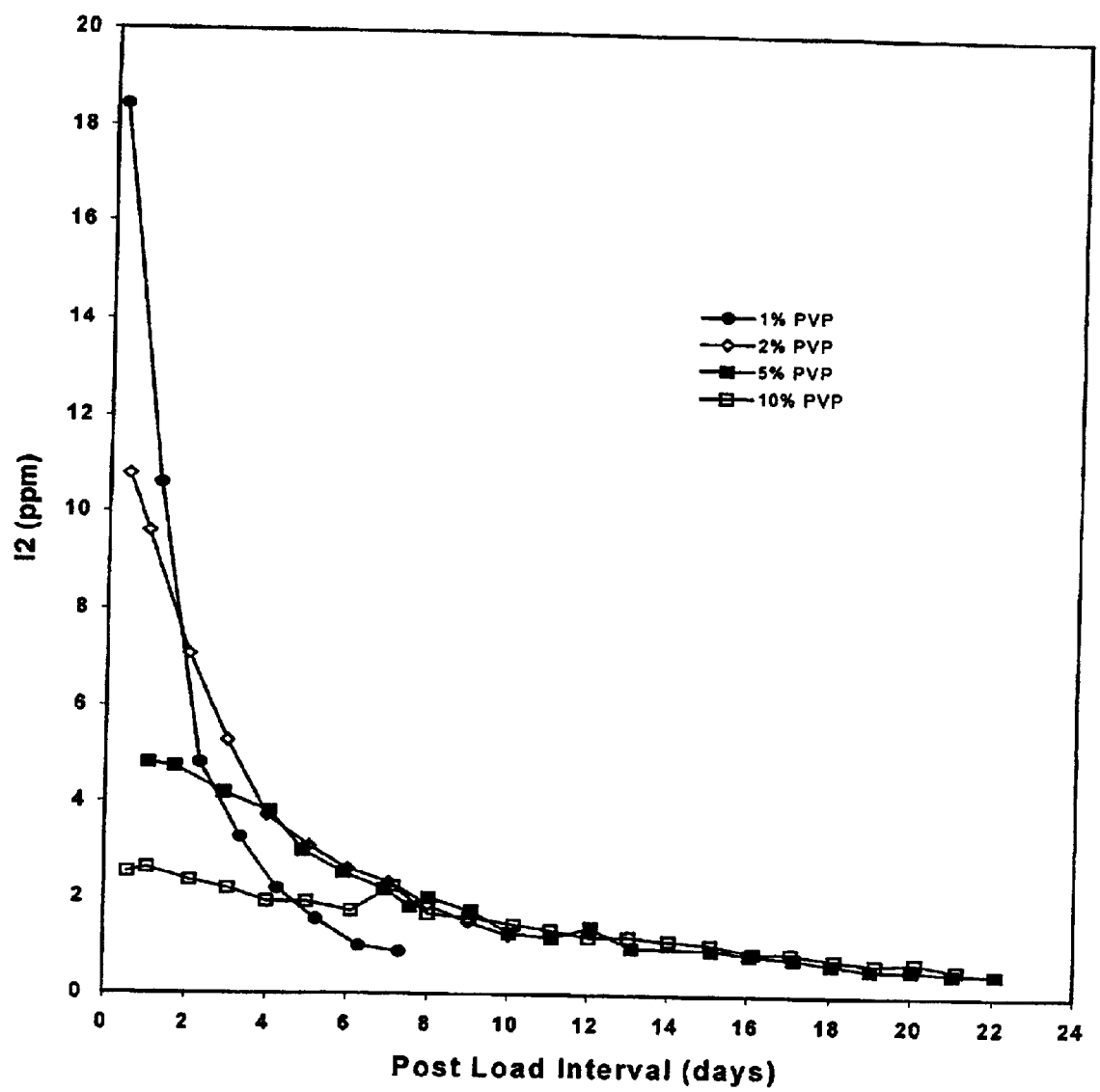
FIG. 16 shows the egress rates of elemental iodine from an ICAT-Loaded Balloon of a Latex Urinary Catheter versus Concentration of PVP contained within the ICAT formulation.

FIG. 16 shows the effect of varying the concentration of PVP (average molecular weight, 40,000) made up in Part A of an ICAT formulation containing also 60 mM sodium iodide, and a Part B formulation made up as 25 mM sodium iodate, and 25 mM sodium citrate, pH 4.2, mixed in equal volumes with one another to initiate formation of free iodine. The final volume of the ICAT mixture injected through the Luer-lock in inflating the catheter balloon was 10 ml. The balloon was then submerged under 100 ml of 10 mM sodium iodide, and the egress of free iodine trapped as a tri-iodide complex in the external solution, then measured spectroscopically at 350 nm against iodine standards also prepared in the same 10 mM sodium iodide solution used to trap egressing free iodine. At each point, the catheter was rinsed and submerged in a fresh 100 ml of sodium iodide, so that at approximately 24 hour intervals over the course of 22 days the egress rate of free iodine was tracked. As can be seen in FIG. 16, increasing the concentration of PVP from 1% to a high of 10% (weight per unit volume) within the ICAT formulations resulted in a flattening of the peak egress rate of free iodine from the external walls of the balloon (evident by the recovery of free iodine in the solution bathing the balloon), and a shift of the peaks progressively to the right This aspect has the benefit of preserving a sustained rate of free iodine egress over a longer interval with a single loading of the catheter balloon, sustaining anti-infective activity through continuous release of free iodine over longer treatment intervals. Beyond 8 to 10 days, the egress rates for free iodine in PVP fortified ICAT solutions was far less dependent upon PVP concentration, reaching a final equilibrium condition beyond 10 days between about 1 and 2 ppm per 100 ml sodium iodide bathing solution.

In the preferred embodiment the final concentration of PVP should be adjusted to about 2% by weight in ICAT formulations generating free iodine de novo, but may range from a low of about 1% to a high of about 10% by weight per unit volume of ICAT solution. Other iodine binding agents may also be used wherein the fundamental principle of extending the egress rate of free iodine from the external walls of the urinary balloon catheter is retarded by the presence of equilibrium reservoirs within the interior of the balloon competing with equilibrium reservoirs outside the balloon. In this embodiment, outside the balloon includes the walls of the balloon where it is no longer possible for iodine, once crossing into this region, to bind to the binding agent contained within the ICAT solution held within the balloon interior. In an alternative embodiment, a binding agent may be provided in the wall of the balloon or as a coating thereon. Although discussed in terms of a binding agent within an interior of a balloon, it should be understood that the ICAT formulations having a binding agent may be provided within the interior of a variety of catheter or medical device components, such as a catheter shaft, as discussed herein.

It is claimed:

1. A method of providing anti-infective activity to a medical device, comprising:
   a) providing a medical device that is at least in part within a patient; then
   b) delivering an oxidant generating formulation to the medical device, thereby exposing the medical device to an anti-infective oxidant; and
   c) transferring the anti-infective oxidant into a wall of the medical device.

2. The method of claim 1, wherein the medical device has a lumen, and including exposing a wall defining the lumen to the anti-infective oxidant.

3. The method of claim 2, wherein the medical device is a catheter having a shaft defining the lumen and having a balloon with an interior in fluid communication with the lumen of the catheter shaft, and including exposing an inner surface of the balloon to the anti-infective oxidant.

4. The method of claim 2, wherein the oxidant generating formulation that generates the oxidant is delivered into the lumen of the medical device.

5. The method of claim 4, including inserting a tubular delivery member, into the lumen of the medical device, the tubular delivery member having a lumen configured to deliver the oxidant generating formulation into the lumen of the medical device.

6. The method of claim 4, including, after step (c), removing the oxidant generating formulation from the lumen of the medical device.

7. The method of claim 4, including inhibiting expulsion of the oxidant generating formulation from the lumen of the medical device by providing a viscosity increasing hydrogel in the oxidant generating formulation.

8. The method of claim 4, wherein the anti-infective oxidant comprises elemental iodine, and including combining a first solution comprising an iodide and a second solution comprising an iodate such that an elemental iodine generating formulation is produced, and delivering the elemental iodine generating formulation to the lumen of the medical device.

9. The method of claim 4, wherein the anti-infective oxidant comprises elemental iodine and the oxidant generating formulation comprises an iodide and an oxidoreductase, and including exposing the oxidoreductase to a substrate to generate protons or an iodide oxidizing agent, so that the oxidant generating formulation produces elemental iodine.

10. The method of claim 9, including exposing the medical device to a body fluid having the substrate to generate protons or an iodide oxidizing agent, so that the oxidant generating formulation produces elemental iodine when contacted with the body fluid.

11. The method of claim 4, wherein the anti-infective oxidant comprises elemental iodine and the oxidant generating formulation comprises an iodate, and including exposing the iodate to a reducing agent to generate elemental iodine.

12. The method of claim 2, including inserting an oxidant releasing member into the lumen of the medical device.

13. The method of claim 12, wherein the oxidant releasing member has an elongated body configured to be slidably inserted into the lumen of the medical device, and further including, before step (b), exposing the oxidant releasing member to a formulation which generates the oxidant so that the oxidant diffuses into the oxidant releasing member.

14. The method of claim 13, wherein the anti-infective oxidant comprises elemental iodine, and including exposing the oxidant releasing member to an elemental iodine generating formulation comprising an iodide, and iodate and a proton source.

15. The method of claim 14, including transferring about 2 ppm to about 300 ppm of the oxidant from an exterior surface of the medical device to the patient.

16. The method of claim 1, including, after step (c), diffusing the oxidant to an outer surface of the medical device.

17. The method of claim 1, wherein the anti-infective oxidant comprises elemental iodine, and including transferring about 2 ppm to about 300 ppm of the elemental iodine from an exterior surface of the medical device to the patient.

18. The method of claim 1, including transferring the anti-infective oxidant within about 1 to about 30 minutes.

19. The method of claim 1, wherein the anti-infective oxidant is elemental iodine, and including preventing the binding of the elemental iodine within the wall of the medical device.

20. The method of claim 19, wherein the binding of the elemental iodine is prevented by providing a medical device which is free of iodine binding agents.

21. The method of claim 4, wherein the formulation includes a binding agent which is bindable to the anti-infective oxidant, and including binding an amount of the generated anti-infective oxidant to the binding agent to thereby inhibit transfer of the bound anti-infective oxidant into the medical device wall.

22. The method of claim 21, wherein the binding agent is selected from the group consisting of silicone oil, mineral oil, cadexomers, and polyvinylpyrrolidone, and including increasing a duration over which at least about 2 ppm of the anti-infective oxidant is transferred into the medical device wall.

23. The method of claim 21, wherein the anti-infective oxidant comprises elemental iodine, the binding agent comprises polyvinylpyrrolidone, and the polyvinylpyrrolidone is about 1% to about 10% weight per unit volume of the formulation, and including increasing a duration over which at least about 2 ppm of the elemental iodine is transferred from an exterior surface of the medical device to the patient.

24. The method of claim 4, including positioning an insert member into the lumen of the medical device to thereby reduce the amount of formulation delivered into the medical device lumen.

25. An anti-infective oxidant releasing member, comprising an elongated body configured to be slidably disposed within a lumen of a medical device and an anti-infective oxidant releasably contained within the elongated body.

26. The anti-infective oxidant releasing member of claim 25, wherein the elongated body comprises a solid rod.

27. The anti-infective oxidant releasing member of claim 26, wherein the solid rod further includes at least one channel on an outer surface of the rod configured to allow fluid flow therein.

28. The anti-infective oxidant releasing member of claim 25, wherein an outer diameter of the elongated body is about 90% to about 5% less than an inner diameter of the lumen of the medical device.

29. The anti-infective oxidant releasing member of claim 25, wherein an outer diameter of the elongated body is about 20% less than an inner diameter of the lumen of the medical device.

30. The anti-infective oxidant releasing member of claim 25, wherein the oxidant comprises elemental iodine.

31. The anti-infective oxidant releasing member of claim 26, wherein the elongated body is formed of a polymeric material, and wherein elemental iodine is diffusible within the polymeric elongated body.

32. A method of providing anti-infective activity to a medical device, comprising:
   a) exposing the medical device to a solution that produces an anti-infective oxidant by inserting an anti-infective oxidant releasing member into the device; and
   b) transferring a sufficient amount of anti-infective oxidant into a wall of the medical device to provide the medical device with anti-infective activity.

33. The method of claim 32, wherein the solution is aqueous and the anti-infective oxidant is elemental iodine.

34. The method of claim 33, wherein the aqueous solution produces at least about 0.1 ppm of elemental iodine.

35. The method of claim 33, including transferring about 2 ppm to about 300 ppm of the elemental iodine from an exterior surface of the medical device to a patient.

36. The method of claim 35, wherein step (a) further comprises exposing the medical device a single time to the aqueous solution.

37. The method of claim 36, wherein the aqueous solution produces about 2 ppm to about 10 ppm of iodine.

38. The method of claim 33, including transferring not greater than about 1000 micrograms a day of the elemental iodine from an exterior surface of the medical device to a patient.

39. A method of providing anti-infective activity to a medical device, comprising:
   a) exposing an oxidant releasing member to a formulation that generates an anti-infective oxidant, that diffuses into the oxidant releasing member; and
   b) inserting the anti-infective oxidant releasing member into the medical device so that the anti-infective oxidant diffuses from the oxidant releasing member into a wall of the medical device.

40. A method of providing anti-infective activity to a medical device, comprising:
   a) inserting an anti-infective oxidant releasing member into the medical device, wherein the member is configured to be adjacent to or in the medical device; and
   b) transferring the anti-infective oxidant into a wall of the medical device.

41. The method of claim 40, wherein the medical device is at least in part within a patient.

* * * * *